US005981193A

United States Patent [19]
Harpold et al.

[11] Patent Number: 5,981,193
[45] Date of Patent: *Nov. 9, 1999

[54] HUMAN NEURONAL NICOTINIC ACETYLCHOLINE RECEPTOR COMPOSITIONS AND METHODS EMPLOYING SAME

[75] Inventors: Michael Miller Harpold, El Cajon; Steven Bradley Ellis, San Diego; Paul Brust, San Diego; Michael Akong, San Diego; Gonul Velicelebi, San Diego, all of Calif.

[73] Assignee: Sibia Neurosciences, Inc., La Jolla, Calif.

[*] Notice: This patent is subject to a terminal disclaimer.

[21] Appl. No.: 07/938,154

[22] PCT Filed: Apr. 3, 1991

[86] PCT No.: PCT/US91/02311

§ 371 Date: Nov. 30, 1992

§ 102(e) Date: Nov. 30, 1992

[87] PCT Pub. No.: WO91/15602

PCT Pub. Date: Oct. 17, 1991

Related U.S. Application Data

[63] Continuation-in-part of application No. 07/504,455, Apr. 3, 1990, Pat. No. 5,369,028.

[51] Int. Cl.⁶ .......................... C07K 14/705; C12N 5/10; C12N 15/12
[52] U.S. Cl. .......................... 435/7.1; 435/7.2; 435/69.1; 435/252.3; 435/320.1; 530/350; 436/501; 536/23.5
[58] Field of Search .................. 435/6, 7.1, 7.2, 435/69.1, 252.3, 320.1; 436/507; 514/2; 530/350; 536/23.5

[56] References Cited

U.S. PATENT DOCUMENTS

| | | | |
|---|---|---|---|
| 4,837,148 | 6/1989 | Cregg | 435/172 |
| 4,855,231 | 8/1989 | Stroman et al. | 435/68 |
| 4,859,609 | 8/1989 | Dull et al. | 436/501 |
| 4,882,279 | 11/1989 | Cregg | 435/68 |
| 4,929,555 | 5/1990 | Cregg et al. | 435/172 |
| 4,981,784 | 1/1991 | Evans et al. | 435/6 |
| 5,024,939 | 6/1991 | Gorman | 435/69 |
| 5,071,773 | 12/1991 | Evans et al. | 436/501 |
| 5,091,518 | 2/1992 | Sucov et al. | 536/27 |
| 5,369,028 | 11/1994 | Harpold et al. | 435/252 |
| 5,386,025 | 1/1995 | Jay et al. | 536/24 |
| 5,401,629 | 3/1995 | Harpold et al. | 435/6 |
| 5,436,128 | 7/1995 | Harpold et al. | 435/6 |

FOREIGN PATENT DOCUMENTS

| | | |
|---|---|---|
| 0325849 | 8/1989 | European Pat. Off. . |
| 8803168 | 5/1988 | WIPO . |
| 8909834 | 10/1989 | WIPO . |
| 9010648 | 9/1990 | WIPO . |
| 9106677 | 5/1991 | WIPO . |
| 9115602 | 10/1991 | WIPO . |
| 9202639 | 2/1992 | WIPO . |
| 9513299 | 5/1995 | WIPO . |

OTHER PUBLICATIONS

Anand and Lindstrom, "Nucleotide sequence of the human nicotinic acetylcholine receptor β2 subunit gene," *Nucleic Acids Research*, 18:4272 (1990).

Beeson et al., "The human muscle nicotinic acetylcholine receptor α–subunit exists as two isoforms: a novel exon," *The EMBO Journal* 9:2101–2106 (1990).

Boulter et al., "Functional expression of two neuronal nicotinic acetylcholine receptors from cDNA clones identifies a gene family," *Proc. Natl. Acad. Sci, USA*, 84:7763–7767 (1987).

Boulter et al., "Isolation of a cDNA clone coding for a possible neural nicotine acetylcholine receptor α–subunit," *Nature*, 319:368–374 (1986).

Claudio et al., "Genetic Reconstitution of Functional Acetylcholine Receptor Channels in Mouse Fibroblasts," *Science* 238: 1688–1694 (1987).

Clementi et al., "Pharmacological Characterization of Cholinergic Receptors in a Human Neuroblastoma Cell Line," *Journal of Neurochemistry*, 47:291–297 (1986).

Conti–Tronconi et al., "Brain and muscle nicotinic acetylcholine receptors are different but homologous proteins," *Proc. Natl. Acad. Sci. USA*, 82:5208–5212 (1985).

Couturier et al., "A Neuronal Nicotinic Acetylcholine Receptor Subunit (α7) Is Developmentally Regulated and Forms a Homo–Oligomeric Channel Blocked by α–BTX," *Neuron*, 5:847–856 (1990).

Dascal, "The Use of *Xenopus oocytes* for the study of Ion Channels," *CRC Critical Reviews in Biochemistry*, 22:317–387 (1987).

Deneris et al., "$β_3$: A New Member of Nicotinic Acetylcholine Receptor Gene Family Is Expressed in Brain," *The Journal of Biological Chemistry*, 264:6268–6272 (1989).

Deneris et al., "Pharmacological and functional diversity of neuronal nicotinic acetylcholine receptors," *TIPS*, 12:34–40 (1991).

Deschamps et al., Identification of a Transcriptional Enhancer Element Upstream from the Proto–Oncogene fos, *Science*, 230:1174–1178 (1995).

Doolittle, *OF URFS AND ORFS*, University Science Books, Mill Valley, 10–15 (1986).

Duvoisin et al., "The Functional Diversity of the Neuronal Nicotinic Acetylcholine Receptors Is Increased by a Novel Subunit: β4," *Neuron*, 3:487–496 (1989).

(List continued on next page.)

*Primary Examiner*—John Ulm
*Attorney, Agent, or Firm*—Stephanie L. Siedman; Heller Ehrman White & McAuliffe

[57] ABSTRACT

Human neuronal nicotinic acetylcholine receptor subunits are described, as are methods for producing cells containing functional receptors employing such subunits. Also described are assay methods for determining the presence of functional HnAChRs in transfected cells, and for determining the agonist or antagonist activity of compounds with respect to such cells.

41 Claims, 15 Drawing Sheets

OTHER PUBLICATIONS

Fornasari et al., "Molecular cloning of human neuronal nicotinic receptor $\alpha_3$–subunit," *Neuroscience Letters,* 111:351–356 (1990).

Goldman et al., "Members of a Nicotinic Acetylcholine Receptor Gene Family Are Expressed in Different Regions of the Mammalian Central Nervous System," *Cell,* 48:965–973 (1987).

Ishikawa et al., "Acetylcholine Receptors of Human Skeletal Muscle: a Species Difference Detected by Snake Neurotoxins," *Brain Research,* 346:82–88 (1985).

Kurosaki et al., "Functional properties of nicotinic acetylcholine receptor subunits expressed in various combinations," *FEBS Letters,* 214:253–258 (1987).

Larsson et al., "In vitro Binding of $^3$H–Acetylcholine to Nicotinic Receptors in Rodent and Human Brain," *Journal of Neural Transmission,* 69:3–18 (1987).

Lathe, "Synthetic Oligonucleotide Probes Deduced from Amino Acid Sequence Data," *J. Mol. Biol.* 183:1–12 (1985.

Luetje and Patrick, "Both $\alpha$–and $\beta$–subunits Contribute to the Agonist Sensitivity of Neuronal Nicotinic Acetylcholine Receptors," *The Journal of Neuroscience,* 11:837–845 (1991).

Lukas, "Pharmacological Distinctions between Functional Nicotinic Acetylcholine Receptors on the PC12 Rat Pheochromocytoma and the TE671 Human Medulloblastoma," *The Journal of Pharmacology and Experimental Therapeutics* 251:175–182 (1989).

Marshall et al., "Sequence and functional expression of a single $\alpha$subunit of an insect nicotinic acetylcholine receptor," *The EMBO Journal,* 9:4391–4398 (1990).

Nef et al., "Genes expressed in the brain define three distinct neuronal nicotinic acetylcholine receptors," *The EMBO Journal,* 7:595–601 (1988).

Patrick et al., "Acetylcholine Receptor Metabolism in a Nonfusing Muscle Cell Line," *The Journal of Biological Chemistry,* 252:2143–2153 (1977).

Quik and Geertsen, "Neuronal nicotinic $\alpha$–bungarotoxin sites," *Can. J. Physiol. Pharmacol.,* 66:971–979 (1988).

Schoepfer et al., "The human medulloblastoma cell line TE671 expresses a muscle–like acetylcholine receptor," *FEBS Letters,* 226:235–240 (1988).

Stroud et al., "Nicotinic Acetylcholine Receptor Superfamily of Ligand–Gated Ion Channels," *Biochemistry,* 29:11009–11023 (1990).

Subramani et al., "Expression of the Mouse Dihydrofolate Reductase Complementary Deoxyribonucleic Acid in Simian Virus 40," *Molecular and Cellular Biology,* 1:854–864 (1981).

Sugaya et al., "Nicotinic Acetylcholine Receptor Subtypes in Human Frontal Cortex: Changes in Alzheimers'Disease," *Journal of Neuroscience Research* 27:349–359 (1990).

Tanabe, et al., "A Family of Metabotropic Glutamate Receptors," *Neuron,* 8:169–179 (1992).

Wada et al., "Distributrion of Alpha2, Alpha3, Alpha4, and Beta2 Neuronal Nicotinic Receptor Subunit mRNAs in the Central Nervous System: A hybridization of Histochemical Study in the Rat," *The Journal of Comparative Neurology,* 284:314–335 (1989).

Wada et al., "Functional Expression of a New Pharamcological Subtype of Brain Nicotinic Acetylcholine Receptor," *Science,* 240:330–334 (1988).

Wood, "Gene Cloning Based on Long Oligonucleotide Probes," *Methods in Enzymology,* 152:443–447 (1987).

Akong et al., Characterization of nicotinic acetylcholine receptor in a human neuroblastoma cell line, *FASEB J.,* 4(3):A737 (1990).

Alam et al.,Reporter Genes: Application to the study of mammalian gene transcription, *Anal. Biochem.* 188:245–254 (1990).

Allard, et al., Sequence of the gene encoding the human M1 muscarinic acetylcholine receptor, *Nucl. Acids Res.* 15:10604 (1987).

Alton and Vapnek, Nucleotide sequence analysis of the chloramphenicol resistance transposon Tn9, *Nature* 282:864–869 (1979).

Anand et al., Nucleotide sequence of the human nicotinic acetylcholine receptor $\beta_2$ subunit gene, *Nucleic Acids Res.* 18914):4272 (1990).

Anand et al., Neuronal nicotinic acetylcholine receptors expressed in *Xenopus oocytes* have a pentameric quanternary structure, *J. Biol. Chem.* 266(17):11192–11198 (1991).

Baldwin et al., Cloning of the luciferase structural genes from *Vibrio harveyi* and expression of bioluminescence in *Escherichia coli, Biochemistry* 23:3663–367 (1984).

Ballivet et al., Electrophysiology of a chick neuronal nicotinic acetylcholine receptor expressed in *Xenopus oocytes* after cDNA injection, *Neuron* 1:847–852 (1988).

Beeson et al., The human muscle nicotinic acetylcholine receptor $\alpha$–subunit exists as two isoforms: a novel exon, *EMBO J.* 9(7):2101–2106 (1990).

BIOSIS abstract #87125524, Bartel et al., Growth factors and membrane depolarization activate distinct programs of early response gene expression dissociation of fos and jun induction, *Genes Dev.* 3(3):304–313 (1989).

BIOSIS abstract #88119253, Levy et al., Cytoplasmic activation of ISGF3 the positive regulator of interferon–alpha–stimulated transcription reconstituted in vitro, *Genes Dev.* 3(9):1362–1371 (1989).

BIOSIS abstract #88127139, Nishizuka et al., The family of protein kinase C for signal transduction, *J. Am. Med. Assoc.* 262(13):1826–1833 (1989).

Blackshear et al., Protein kinase C–dependent and –independent pathways of proto–oncogene induction in human astrocytoma cells, *J. Biol. Chem.* 262(16):7774–7781 (1987).

Blanchard et al., The regulatory stategies of c–myc and c–fos proto–oncogenes share some common mechanisms, *Biochimie* 70:877–884 (1988).

Bonner et al., Cloning and expression of the human and rat m5 muscarinic acetylcholine receptor genes, *Neuron* 1:403–410 (1988).

Bonnieu et al., Requirements for c–fos mRNA down regulation in growth stimulated murine cells, *Oncogene* 4:881–888 (1989).

Bouche, Basic fibroblast growth factor enters the nucleolus and stimulates the transcription of ribosomal genes in ABAE cells undergoing $G_0$–$G_1$ transition, *Proc. Natl. Acad. Sci. USA* 84:6770–6774 (1987).

Boulter et al., Isolation of a cDNA clone coding for a possible neural nicotinic acetylcholine receptor $\alpha$–subunit, *Nature* 319:368–374 (1986).

Boulter et al., Functional expression of two neuronal nicotinic acetylcholine receptors from cDNA clones identifies a gene family, *Proc. Natl. Acad. Sci. USA* 84:7763–7767 (1987).

Boulter et al., α3, α5, and β4: Three members of the rat neuronal nicotinic acetylcholine receptor–related gene family form a gene cluster, *J. Biol. Chem.* 265:4472–4482 (1990).

Boulter et al., Rat nicotinic acetylcholine receptor alpha 6 mRNA sequence, unpublished (1993) GENBANK Accession #L08227.

Bunzow et al., Cloning and expression of a rat $D_2$ dopamine receptor cDNA, *Nature* 336:783–787 (1988).

Changelian et al., Structure of the NGFI–A gene and detection of upstream sequences responsible for its transcriptional induction by nerve growth factor, *Proc. Natl. Acad. Sci. USA* 86:377–381 (1989).

Chavez–Noriega et al., Characterization of recombinant human neuronal nicotinic ACH receptors expressed in HEK293 cells and *Xenopus oocytes*, *Soc. Neurosci. Abstr.* (1995).

Claudio et al., Genetic reconstitution of functional acetylcholine receptor channels in mouse fibroblasts, *Science* 238:1688–1694 (1987).

Clementi et al., Pharmacological characterization of cholinergic receptors in a human neuroblastoma cell line, *J. Neurochem.* 47(1):291–297 (1986).

Cleveland et al., Number and evolutionary conservation of the α–and βtubulin and cytoplasmic β–and γ–actin genes using specific cloned cDNA probes, *Cell* 20:95–105 (1980).

Collins et al., cAMP stimulates transcription of the $β_2$–adrenergic receptor gene in response to short–term agonist exposure, *Proc. Natl. Acad. Sci. USA* 86:4853–48576 (1989).

Comb et al., A cyclic AMP–and phorbol ester–inducible DNA element, *Nature* 323:353–356 (1986).

Conti–Tronconi et al., Brain and muscle nicotinic acetylcholine receptors are different but homologous proteins, *Proc. Natl. Acad. Sci. USA* 82:5208–5212 (1985).

Cotecchia et al., Multiple second messenger pathways of a α–adrenergic receptor subtypes expressed in eukaryotic cells, *J. Biol. Chem.* 265(1):63–69 (1990).

Couturier et al., A neuronal nicotinic acetylcholine receptor subunit (α7) is developmentally regulated and forms a homo–oligomeric channel blocked by α–BTX, *Neuron* 5:847–856 (1990).

Curran et al., Barium modulates c–fos expression and post-–transcriptional modification, *Proc. Natl. Acad. Sci. USA* 83:8521–8524 (1986).

Curran et al., FBJ murine osteosarcoma virus: Identification and molecular cloning of biologically active proviral DNA, *J. Virology* 44(2):674–682 (1982).

Dascal, The use of *Xenopus oocytes* for the study of ion channels, *CRC Crit. Rev. Biochem.* 22(4):317–387 (1987).

Deneris et al., Primary structure and expression of β2: A novel subunit of neuronal nicotinic acetylcholine receptors, *Neuron* 1:45–54 (1988).

Deneris et al., Pharmacological and functional diversity of neuronal nicotinic acetylcholine receptors, *Trends Pharmacol. Sci.* 12:34–40 (1991).

Deneris et al., $β_3$: A new member of nicotinic acetylcholine receptor gene family is expressed in brain, *J. Biol. Chem.* 264(11):6268–6272 (1989).

Denhardt, A membrane–filter technique for the detection of complementary DNA, *Biochem. Biophys. Res. Commun.* 23:641–646 (1966).

Devreotes, *Dictyostelium discoideum*: A model system for cell–cell interactions in development, *Science* 245:1054–1058 (1989).

deWet et al., Firefly luciferase gene: Structure and expression in mammalian cells, *Mol. Cell. Biol.* 7:725–737 (1987).

Dixon et al., Cloning of the gene and cDNA for mammalian β–adrenergic receptor and homology with rhodopsin, *Nature* 321:75–79 (1986).

Doolittle, *Of URFS and ORFS. A Primer on How to Analyze Dervied Amino Acid Sequences,* selected pages, University Science Books, Mill Valley, CA (1986).

Duvoisin et al., The functional diversity of the neuronal nicotinic acetylcholine receptors is increased by a novel subunit: β4, *Neuron* 3:487–496 (1989).

Elliott et al., Cloning and functional expression of human neuronal nicotinic acetylcholine receptor subunits α2, α3, α4, α7, β2 and β4, *Soc. Neurosci Abstr.* 19(1–3):69 (1993).

Ellis et al., Replacement of insulin receptor tyrosine residues 1162 and 1163 compromises insulin–stimulated kinase activity and uptake of 2–deoxyglucose, *Cell* 45:721–732 (1986).

Ellis et al., Sequence and expression of mRNAs encoding the $α_1$ and $α_2$ subunits of a DHP–sensitive calcuim channel, *Science* 241:1661–1664 (1988).

EMBASE abstract #87032747, Gonda et al., A molecular basis for growth regulation in normal and neoplastic hemopoiesis, *Cancer Rev.(Denmark)* 3:58–90 (1986).

EMBASE abstract #90361366, Roux et al., Nuclear localization of c–fos, but not v–fos proteins, is controlled by extracellular signals, *Cell* 63(2):341–351 (1990).

Engebrecht and Silverman, Identification of genes and gene products necessary for bacterial bioluminescene, *Proc. Natl. Acad. Sci. USA* 1:4145–4158 (1984).

Fanger et al., Differential expression of sodium channels and nicotinic acetylcholine receptor channels in nnr variants of the PC12 pheochromocytoma cell line, *J. Membrane Biol.* 144:71–80 (1995).

Fink et al., The CGTCA sequence motif is essential for biological activity of the vasoactive intestinal peptide gene cAMP–regulated enhancer, *Proc. Natl. Acad. Sci. USA* 85:6662–6666 (1988).

Firtel et al., G protein linked signal transduction pathways in development: Dictyostelium as an experimental system, *Cell* 58:235–239 (1989).

Fornasari et al., Molecular cloning of human neuronal nicotinic receptor α3–subunit, *Neurosci. Lttrs.* 111:351–356 (1990).

Frielle et al., Cloning of the cDNA for the human $β_1$–adrenergic receptor, *Proc. Natl. Acad. Sci. USA* 84:7920–7924 (1987).

Gautam et al., A G protein gamma subunit shares homology with ras proteins, *Science* 244:971–974 (1989).

Gilman, G proteins: Transducers of receptor–generated signals, *Ann. Rev. Biochem.* 56:615–649 (1987).

Goldman et al. Members of a nicotinic acetylcholine receptor gene family are expressed in different regions of the mammalian central nervous system, Cell 48:965–973 (1987).

Gorman et al., Recombinant genomes which express chloramphenicol acetyltransferase in neuroblastom cell line reside on different molecules, *Biochem. Biophys. Res. Commun.* 137(3):1141–1147 (1986).

Gotti et al., Acetylcholine operated ion channel and α–bungarotoxin binding site in a human neuroblastoma cell line reside on different molecules, *Biochem. Biophys. Res. Commun.* 137(3):1141–1147 (1986).

Goyal, Muscarinic receptor subtypes, *N. Engl. J. Med.* 321(15):1022–1029 (1989).

Greenberg et al., Stimulation of neuronal acetylcholine receptors induces rapid gene transcription, *Science* 234:80–83 (1986).

Halvorsen et al., Affinity labeling of neuronal acetylcholine receptor subunits with an α–neurotoin that blocks receptor function, *J. Neurosci* 7(8):2547–2555 (1987).

Hamill et al., Improved patch–clamp techniques for high resolution current recording from cells and cell–free membrane patches, *Pflugers Arch.* 391:85–100 (1981).

Herschman, Extracellular signals, transcriptional responses and cellular specificity, *Trends Biochem. Sci.* 14:455–458 (1989).

Hollman et al., Cloning by functional expression of a member of the glutamate receptor family, *Nature* 342:643–648 (1989).

Horwitz et al., Muscarinic receptor stimulation increases inositol–phospholipid metabolism and inhibits cyclic AMP accumulation in PC12 cells, *J. Neurochem.* 53:197–204 (1989).

Ishikawa et al., Acetylcholine receptors of human skeletal muscle: A speices difference detected by snake neurotoxins, *Brain Res.* 346:82–88 (1985).

Jay et al., Primary structure of the γ subunit of the DHP–sensitive calcium channel from skeletal muscle, *Science* 248:490–492 (1990).

Johnson et al., Expression and structure of the human NGF receptor, *Cell* 47:545–554 (1986).

Julius et al., Molecular characaterization of a functional cDNA encoding the serotonin 1c receptor, *Science* 241:558–564 (1988).

Julius et al., The 5HT2 receptor defines a family of structurally distinct but functionally conserved serotonin receptors, *Proc. Natl. Acad. Sci. USA* 87:928–932 (1990).

Kayano et al., Primary structure of rat brain sodium channel III deduced from the cDNA sequence, *FEBS Lttrs.* 228:187–194 (1988).

Klein et al., A chemoattractant receptor controls development in *Dictyostelium discoideum, Science* 241:1467–1472 (1988).

Kobilka et al., Cloning, sequencing, and expression of the gene coding for the human platelet $\alpha_2$–adrenergic receptor, *Science* 238:650–656 (1987).

Kobilka et al., An intronless gene encoding a potential member of the family of receptors coupled to guanine nucleotide regulatory proteins, *Nature* 329:75–79 (1987).

Kurosaki et al., Functional properties of nicotinic acetylcholine receptor subunits expressed in various combinations, *FEBS Lttrs.* 214(2):253–258 (1987).

Lamb et al., Demonstratio in living cells of an intragenic negative regulatory element within the roden c–fos gene, *Cell* 61:485–496 (1990).

Lambert et al., Muscarinic receptor binding characteristics of a human neuroblastoma SK–N–SH and its clones SH–SY5Y and SH–EP1, *Eur. J. Pharmacol.* 165:71–77 (1988).

Larsson et al., In vitro binding of $^3$H–acetylcholine to nicotinic receptors in rodent and human brain, *J. Neural Transm.* 69:3–18 (1987).

Lathe, Synthetic oligonucleotide probes deduced from amino acid sequence data theoretical and practical considerations, *J. Mol. Biol.* 183:1–12 (1984).

Levitan et al., Structural and functional basis for $GABA_a$ receptor heterogeneity, *Nature* 335:76–79 (1988).

Lloyd et al., SIB–1765F, a novel nicotinic agonist: Profile in models of extrapyramidal motor dysfunction, *Soc. Neurosci. Abstr.* (1995).

Luetje et al., Both α–and β–subunits contribute to the agonist sensitivity of neuronal nicotinic acetylcholine receptors, *J. Neurosci.* 11(3):837–845 (1991).

Lukas, Pharmacological distinctions between functional nicotinic acetylcholine receptors on the PC12 rat pheochromocytoma and the TE671 human medulloblastoma, *J. Pharmacol. Exp. Therap.* 251(1):175–182 (1989).

Marshall et al., Sequence and functional expression of a single αsubunit of an insect nicotinic acetylcholine receptor, *EMBO J.* 9(13):4391–4398 (1990).

Marullo et al., Expression of human β1 and β2 adrenergic receptors in *E. coli* as a new tool for ligand screening, *Bio/Technology* 7:923–927 (1989).

Mauron et al., Structure of chicken genes encoding the nicotinic acetylcholine receptor subunits and their variants, *Soc. Neurosci. Abstr.* 17 (1991).

McAllister et al., Establishment of a human medulloblastoma cell line, *Int. J. Cancer* 20:206–212 (1977).

McKinnon, D., Isolations of a cDNA clone coding for a putative second potassium channel indicates the existence of a gene family, *J. Biol. Chem.* 264:8230–8236 (1989).

Mechti et al., Sequence requirements for premature transcription arrest within the first intron of the mouse c–fos gene, *Mol. Cell Biol.* 11(5):2832–2841 (1991).

Menzaghi et al., SIB–1765F: A novel nicotinic agonist with locomotor stimulant properties in rats, *Soc. Neurosci. Abstr.* (1995).

Michel et al., PC12 phaeochoromocytoma cells contain an atypical muscarinic receptor binding site, *Br. J. Pharmacol.* 97:914–920 (1989).

Montminy et al., Identification of a cyclic–AMP–responsive element within the rat somatostatin gene, *Proc. Natl. Acad. Sci. USA* 83:6682–6686 (1986).

Morgan et al., Stimulus–transcription coupling in neurons: Role of cellular immediate–early genes, *Trends Neruosci.* 12(11):459–462 (1989).

Nash et al., Molecular cloning of human neuronal nicotinic acetylcholine receptor subunits, *Neurobiol. Neurochem.* 4(7):A2153 (1990).

Nash et al., Molecular cloning and expression of human neuronal nicotinic acetylcholine receptor subunits, *Soc. Neurosci. Abstr.* 16:10 (1990).

Nef et al., Genes expressed in the brain define three distinct neuronal nicotinic acetylcholine receptors, *EMBO J.* 7(3):595–601 (1988).

Nielsen et al., A highly sensitive, mixed assay for chloramphenicol acetyltransferase activity in transfected cells, *Anal. Biochem.* 179:19–23 (1989).

Noda et al., Expression of functional sodium channels from cloned CDNA, *Nature* 322:826–828 (1986).

Noda et al., Existence of distinct sodium channel messenger RNAs in rat brain, *Nature* 320:188–192 (1986).

Nordeen, Luciferase reporter gene vectors for analysis of promoters and enhancers, *BioTechniques* 6(5):454–456 (1988).

Papke et al., The role of the $\beta_4$–subunit in determining the kinetic properties of rat neuronal nicotinic acetylcholine $\alpha_3$–receptors, *J. Physiol.* 440:95–112 (1991).

Patrick et al., Acetylcholine receptor metabolism in a nonfusing muscle cell line, *J. Biol. Chem.* 252(6):2143–2153 (1977).

Peralta et al., Distinct primary structures, ligand–binding properties and tissue–specific expression of four human muscarinic acetylcholine receptors, *EMBO J.* 6(13):3923–3929 (1987).

Peralta et al., Differential regulation of PI hydrolysis and adenylyl cyclase by mascarinic receptor subtypes, *Nature,* 334:434–437 (1988).

Pritchett et al., Importance of a novel $GABA_A$ receptor subunit for benzodiazepine pharmacology, Nature, 338:582–585 (1989).

Quik et al., Neuronal nicotinic α–bungarotoxin sites, *Can. J. Physiol. Pharmacol.* 66:971–979 (1988).

Rao et al., In vitro characterization of SIB–1765F, a novel nicotinic agonist, *Soc. Neurosci. Abstr.* (1995).

Receptor Genetics, Inc. (file of correspondence with SIBIA).

Revah et al., Mutations in the channel domain alter desensitization of a neuronal nicotinic receptor, *Nature* 353:846–849 (1991).

Riabowol et al., The catalytic subunit of cAMP–dependent protein kinase induces expression of genes contraining cAMP–responsive enhancer elements, *Nature* 336:83–86 (1988).

Ruth et al., Primary structure of the β subunit of the DHP–sensitive calcium channel from skeletal muscle, *Science,* 245:1115–1118 (1989).

Sacaan et al., Effect of (+)–epibatidine on the release of catecholamines: Biochemical and behavioral evidence in rats, *Soc. Neurosci. Abstr.* (1995).

Sassone–Corsi et al., Induction of proto–oncogene fos transcription through the adenylate cyclase pathway: characterization of a cAMP–responsive element, *Genes Dev.* 2:1529–1538 (1988).

Schoepfer et al., The human medulloblastoma cell line TE671 expresses a muscle–like acetylcholine receptor, *FEBS Lttrs.* 226(2):235–240 (1988).

Schoepfer et al., cDNA clones coding for the structural subunit of a chicken brain nicotinic acetylcholine receptor, *Neuron* 1:241–248 (1988).

Schoepfer et al., Brain α–bungartoxin binding protein cDNAs and MAbs reveal subtypes of this branch of the ligand–gated ion channel gene superfamily, *Neuron* 5:35–48 (1990).

Schoepfer et al., *Molecular Biology of Neuroreceptors and Ion Channels* Maclicke, A. (Ed.), NATO–ASI Series, Springer Vergal, Heidelberg (1989).

Schofield et al., Sequence and functional expression of the $GABA_A$ receptor shows a ligand–gated receptor super–family, *Nature* 328:221–227 (1987).

Serra et al., The intact human neuroblastoma cell (SH–Sy5Y) exhibits the high–affinity [$^3$H]pirenzepine binding associated with hydrolysis of a phosphatidylinositols, *J. Neurochem.* 50:1513–1521 (1988).

Serra et al., Phorbol esters alter muscarinic receptor binding and inhibit polyphosphoinositide breakdown in human neuroblastoma (SH–SY5Y) cells, *Biochem. Biophys. Res. Comm.* 140:160–166 (1988).

Sheng et al., The regulation and function of c–fos and other immediate early genes in the nervous system, *Neuron* 4:477–485 (1990).

Shivers B.D., Two novel $GABA_A$ receptor subunits exist in distinct neuronal subpopulations, *Neuron* 3:327–337 (1989).

Short et al., Characterization of the phsophoenolpyruvate carboxykinase (GTP) promoter–regulatory region, *J. Biol. Chem.* 261:9721–9726 (1986).

Stauderman et al., Characterization of recombinant huamn neuronal nicotinic acetylcholine receptor subtypes α4β4 and α4β4 stably expressed in HEK293 cells, *Soc. Neurosci. Abstr.* (1995).

Stillman et al., Replication and supercoiling of simian virus 40 DNA in cell extracts from human cells, *Mol. Cell Biol.* 5:2051–2060 (1985).

Stormann et al., Molecular cloning and expressionof a dopamine D2 receptor from human retina, *Molec. Pharm.* 37:1–6 (1990).

Strader et al., Structural basis of β–adrenergic receptor function, *FASEB J.* 3:1825–1832 (1989).

Stroud et al., Nicotinic acetylcholine receptor superfamily of ligand–gated ion channels, *Biochemsitry* 29(50):11009–11023 (1990).

Stumpo et al., Identification of c–fos sequences involved in induction by insulin and phrobol esters, *J. Biol. Chem.* 263(4):1611–1614 (1988).

Subramani et al., Expression of the mouse dihydrofolate reductase complementary deoxyribonucleic acid in simian virus 40 vectors, *Mol. Cell Biol.* 1:854–864 (1981).

Sugaya et al., Nicotinic acetylcholine receptor subtypes in human frontal cortex: Changes in Alzheimer's disease, *J. Neurosci. Res.* 27:349–359 (1990).

Tanabe et al., Primary structure of the receptor for calcium channel blockers from skeletal muscle, *Nature* ; 328:313–318 (1987).

Tempel et al., Cloning of a probable potassium channel gene from mouse brain, *Nature* 332:837–839 (1988).

Toh et al., Isolation and acharactierzationof a rat liver alkaline phosphatase gene, *Eur. J. Biochem.* 182:231–238 (1989).

Urlaub et al., Effect of gamma rays at athe dihydrofolate reductase locus: Deletions and inversion, *Somatic Cell. Molec. Genet.* 12(6):555–566 (1986).

Verma et al., Proto–oncogene fos: Complex but versatile regulation, *Cell* 51:513–514 (1987).

Vernallis et al., ACHR gene products in chick ciliary ganglia: Transcripts, subunits, and receptor subtypes, *Soc. Neurosci. Abstr.* 17:23 (1991).

Visvader et al., Two adjacent promoter elements mediate nerve growth factor activation of the c–fos gene and bind distinct nuclear complexes, *Proc. Natl. Acad. Sci. USA* 85:9474–9478 (1988).

Wada et al., Functional expressionof a new pharmacological subtype of brain nicotinic acetylcholine receptor, *Science* 240:330–334 (1988).

Wada et al., Distribution of Alpha2, Alpha 3, Alpha4, and Beta2 neuronal nicotinic receptor subunit mRNAs in the central nervous system: A hybridiztaion histochemical study in the rat, *J. Comp. Neurol.* 284:314–335 (1989).

Whiting et al., Structurally different neuronal nicotinic acetylcholine receptor subtype purified and characterized using monoclonal antibodies, *J. Neurosci.* 7(12):4005–4016 (1987).

Whiting et al., Purification and characterization of a nicotinic acetylcholine receptor from rat brain, *Proc. Natl. Acad. Sci. USA* 84:595–599 (1987).

Whiting et al., Affinity labelling of neuronal acetylcholine receptors localizes acetylcholine–binding sites to their β–subunits, *FEBS Lttrs.* 213(1):55–60 (1987).

Whiting et al., Expression of nicotinic acetylcholine receptor subtypes in brain and retina, *Mol. Brain Res.* 10:61–70 (1991).

Whiting et al., Structural and pharmacological characterization of the major brain nicotinic acetylcholine receptor subtype stably expressed in mouse fibroblasts, *Mol. Pharmacol.* 40:463–472 (1991).

Wigler et al., DNA–mediated transfer of the adrenine phosphoribosyltransferase locus into mammalian cells, *Proc. Natl. Acad. Sci. USA* 76:1373–1376 (1979).

Wilson et al., Inhibitory action of nicotinic antagonists on transmitter release at the neuromuscular junction of the rat, *Neurosci. Lttrs.* 186:29–32 (1995).

Yeh et al., Ultrastructural localization of a platelet–derived growth factor/ v–sis–related protein(s) in cytoplasm and nucleus of simian sarcoma virus–transformed cells, *Proc. Natl. Acad. Sci. USA* 84:2317–2321 (1987).

Ymer et al., $GABA_A$ receptor β subunit heterogeneity: functional expressionof cloned cDNAs, *EMBO J.* 8:1665–1670 (1989).

Young et al., Isolation and characterization of a new cellular oncogene encoding a protein with multiple potential transmembrane domains, *Cell* 45:711–719 (1986).

Zipser et al., Mapping functional domains in the promoter region of the herpes thymidine kinase gene, *Proc. Natl. Acad. Sci. USA* 78(10):6276–6280 (1981).

EMBO, J, (:771–776, Mauer 1990 Grenningloh et al. Alpha subunit variants of the human glycine receptor: primary structures, functional expression . . .

FEB 244:361–364, Feb. 1989, Schofield et al., Sequence and Expression of human $GABA_A$ receptor and B1 Exhautis.

Nature 305:818–823, COt. 1983, Wada et al., Cloning and sequence analysis of calf DNA and naval genosa DNA encoding α–subunit . . . .

Science 234:80–83, Oct. 1986, Greenberg et al., Stimulation of neuronal acetylcholine receptors induces rapid gene transcription.

Whiting et al, *J. Neuroscience* 8(9):3375–3404, Sep. 1988.

FIG. I

```
195 ...........GCTAAACAGGAGTGGAGCGACTACAAACTGCGCTGGAAC 157
              ||  ||||||  ||||    ||||||||  ||||||||||  ||
              ||  ||||||  ||||    ||||||||  ||||||||||  ||
251 CCAATGTCTGGCTAAAGCAGGAATGGAATGACTACAAGCTGCGCTGGAC 300

156 CCCGCTGATTTTGGCAACATCACATCTCTCAGGGTCCCTTCTGAGATGAT 107
    ||  ||||||  ||||||||    ||||  ||  ||    |  ||||||||  ||||||||
    ||  ||||||  ||||||||    ||||  ||  ||    |  ||||||||  ||||||||
301 CCGGCTGAGTTTGGCAATGTCACCTCCCTGCGCGTCCCTTCAGAGATGAT 305

BamHI
106 CT GGATCC CCGACATTGTTCTCTACAACAA...AAATGGGGAGTTTGCAG 60
    || |||||||| ||||||||  ||||||||||     |  ||||||||||||||  |
    || |||||||| ||||||||  ||||||||||     |  ||||||||||||||  |
351 CT GGATCC CAGACATTGTCCTCTACAACAATGCAGATGGGGAGTTTGCGG 400

59 TGACCCACATGACCAAGGCCCACCTCTTCTCCACGGGCACTGTGCACTGG 10
   |||||||||||||||||||  ||||||||  ||||||||||||||||||||
   |||||||||||||||||||  ||||||||  ||||||||||||||||||||
401 TGACCCACATGACCAAGGCTCACCTCTTCTTCACGGGCACTGTGCACTGG 450

9  GTGCCCCCC
   ||||||||
   ||||||||
451 GTGCCCCCA
```

FIG. 7A

```
  1  CCCCTTCGACCAGCAGAACTGCAAGATGAAGTTTGGCTCCTGGACTTATG   50
     ||||||||||||||||||||||||||||||||||||||||||||| ||||
     ||||||||||||||||||||||||||||||||||||||||||||| ||||
501  CCCCTTCGACCAGCAGAACTGCAAGATGAAGTTTGGCTCCTGGACATATG  550

51  ACAAGGCCAAGATCGACCTGGAGCAGATGGAGCAGACTGTGGACCTGAAG  100
     ||||||||||||||| ||||||||||||| ||| ||||||||||||||||
     ||||||||||||||| ||||||||||||| ||| ||||||||||||||||
551  ACAAGGCCAAGATCGATCTGGAGCAGATGGAGAGGACAGTGGACCTGAAG  600

101  GACTACTGGGAGAGCGGCGAGTGGGCCATCGTCAATGCCACGGGCACCTA  150
     ||||||||||||| |||||||||||||| |||||||||||| || |||||
     ||||||||||||| |||||||||||||| |||||||||||| || |||||
601  GACTACTGGGAGAGTGGCGAGTGGGCCATTATCAATGCCACCGGAACCTA  650

151  CAACAGCAAGAAGTACGACTGCTGCGCCGAGATCTACCCCGACGTCACCT  200
     |||||  |||||||||||||||||||| |||||||||||||| |||||||
     |||||  |||||||||||||||||||| |||||||||||||| |||||||
651  TAACAGTAAGAAGTACGACTGCTGCGCGGAGATCTACCCCGATGTCACCT  700

201  AG................................................  202
     |
     |
701  ACTACTTTGTGATCCGGCGGCTGCCGCTGTTCTATACCATCAACCTCATC  750
```

FIG. 7B

```
  1    ....................CTGGCAGCAGAGGCTGAGCACCGTCTATTTG    31
                           ||  ||||  |||||||||||  ||  ||
                           ||  ||||  |||||||||||  ||  ||
 51    GATGCTGCTGCCAGCGGCCAGTGCCTCAGAAGCTGAGCACCGCCTGTTCC   100

32    AGCGGCTGTTTGAAGATTACAATGAGATCATCCGGCCTGTAGCCAACGTG    81
       ||   |||||  ||||||||||||  ||||||||||||||  ||  ||  |||
       ||   |||||  ||||||||||||  ||||||||||||||  ||  ||  |||
101    AGTACCTGTTCGAAGATTACAACGAGATCATCCGGCCAGTGGCTAATGTG   150

.PvuII   .
 82    TCTGACCCAGTCATCATCCATTTCGAGGTGTCCATGTCT[CAGCTG]GTGAA   131
       ||  |  |||||||||||||||  ||||||||||||||||||||||||
       ||  |  |||||||||||||||  ||||||||||||||||||||||||
151    TCCCATCCAGTCATCATCCAGTTTGAGGTGTCCATGTCT[CAGCTG]GTGAA   200

132    GGTGGATGAAGTAAACCAGATCATGGAGACCAACCTGTGGCTCAAGCAAA   181
       ||||||||||||||||||||||||||||  |||||||||||||  |||||||
       ||||||||||||||||||||||||||||  |||||||||||||  |||||||
201    GGTGGATGAAGTAAACCAGATCATGGAAACCAACCTGTGGCTGAAGCAAA   250

182    TCTGGAATGACTACAAGCTGAAGTGGAACCCCTCTGACTATGGTGGGGCA   231
       |||||||||||||||||||||||  |||||  |||||||||||     ||||
       |||||||||||||||||||||||  |||||  |||||||||||     ||||
251    TCTGGAATGACTACAAGCTGAAATGGAACCCTCTGACTACCAAGGGGTG   300

BglII            .
232    GAGTTCATGCGTGTCCCTGCACAGA[AGATCT]GGAAGCCAGACATTGT...   278
       ||||||||||||||  ||||||| |||||||||||  |||||||||  ||
       ||||||||||||||  ||||||| |||||||||||  |||||||||  ||
301    GAGTTCATGCGTGTTCCTGCAGAGA[AGATCT]GGAAACCAGACATCGTACT   350
```

FIG. 8A

```
  1   .....................TTCCAGGTGGACGACAAGACCAAAGCCT    28
                           |||||||||||| ||||||||||||||||
                           |||||||||||| ||||||||||||||||
351   GTACAACAACGCTGATGGGGATTTCCAGGTGGATGACAAGACCAAAGCTC   400

29   TACTCAAGTACACTGGGGACGTGACTTGGATACCTCCGGCCATCTTTAAG    78
      |||||||||||| || || |||||||||| || |||||||||||||||||
      |||||||||||| || || |||||||||| || |||||||||||||||||
401   TACTCAAGTACACAGGAGAAGTGACTTGGATCCCGCCGGCCATCTTTAAG   450

SacI
 79   AGCTCCTGTAAAATCGACGTGACCTACTTCCCGTTTGATTACCAAAACTG   128
      |||||  || |||||||||||||||||||||||| || || |||||||||
      |||||  || |||||||||||||||||||||||| || || |||||||||
451   AGCTCATGCAAAATCGACGTGACCTACTTCCCATTCGACTACCAAAACTG   500

129   TACCATGAAGTTCGGTTCCTGGTCCTACGATAAGGCGAAAATCGATCTGG   178
       |||||||||||||| ||||||||||||||||| |||| || ||||| ||||
       |||||||||||||| ||||||||||||||||| |||| || ||||| ||||
501   CACCATGAAGTTCGGCTCCTGGTCCTACGACAAGGCAAAGATCGACCTGG   550

179   TCCTGATCGGCTCTTCCATGAACCTCAAGGACTATTGGGAGAGCGGCGAG   228
      |||| |||||||| |||||||||||||||||||||| |||||| ||||||
      |||| |||||||| |||||||||||||||||||||| |||||| ||||||
551   TCCTCATCGGCTCCTCCATGAACCTCAAGGACTACTGGGAGAGTGGCGAG   600

229   TGGGCCATCATCAAAGCCCCAGGCTACAAACACGACATCAAGTACAACTG   278
      ||||| |||||| |||||||| |||||||||| || |||||||||||||
      ||||| |||||| |||||||| |||||||||| || |||||||||||||
601   TGGGCTATCATTAAAGCCCCGGGCTACAAACATGAAATCAAGTACAACTG   650

279   CTGCGAGGAGATCTACCCCGACATCAC......................   305
      ||| |||||||||||||   ||||||||
      ||| |||||||||||||   ||||||||
651   CTGTGAGGAGATCTACCAAGACATCACGTACTCGCTGTACATCCGTCGCC   700
```

FIG. 8B

```
  1  ATGCCCGCTGGCATGGCCCGGCGCTGCGGCCCCGTGGCGCTGCTCCTTGG   50
     ||||   |||  ||||||||  |||  || |    | |   ||||||||| ||        |
     ||||   |||  ||||||||  |||  || |    | |   ||||||||| ||        |
  1  ATGCTGGCTTGCATGGCCGGGCACTCCAACTCAATGGCGCTGTTC...AG   47

51  CTTCGGCCTCCTCCGGCTGTGCTCAGGGGTGTGGGGTACGGATACAGAGG  100
     ||||  ||||  ||    ||||||||||||||||||  |  |||  || ||  |||||||
     ||||  ||||  ||    ||||||||||||||||||  |  |||  || ||  |||||||
 48  CTTCAGCCTTCTTTGGCTGTGCTCAGGGGTTTTGGGAACTGACACAGAGG   97

101  AGCGGCTGGTGGAGCATCTCCTGGATCCTTCCCGCTACAACAAGCTTATC  150
     |||||||  ||||||||||||  |  |||||  |||||||  ||||||||  ||
     |||||||  ||||||||||||  |  |||||  |||||||  ||||||||  ||
 98  AGCGGCTAGTGGAGCATCTCTTAGATCCCTCCCGCTATAACAAGCTGATT  147

151  CGCCCAGCCACCAATGGCTCTGAGCTGGTGACAGTACAGCTTATGGTGTC  200
     ||  ||||||  ||  ||  ||||||||||||||||||||||  |||||||||  |||||  ||
     ||  ||||||  ||  ||  ||||||||||||||||||||||  |||||||||  |||||  ||
148  CGTCCAGCTACTAACGGCTCTGAGCTGGTGACTGTACAGCTCATGGTATC  197

201  ACTGGCCCAGCTCATCAGTGTGCATGAGCGGGAGCAGATCATGACCACCA  250
     |  ||||  |||||||||  |||||||  ||||||||||||||||||||||||||||||
     |  ||||  |||||||||  |||||||  ||||||||||||||||||||||||||||||
198  ATTGGCTCAGCTCATTAGTGTGCACGAGCGGGAGCAGATCATGACCACCA  247

251  ATGTCTGGCTGACCCAGGAGTGGGAAGATTATCGCCTCACCTGGAAGCCT  300
     ||||||||||||||||||||||||||||||||||||||||  ||||||||  ||||||||
     ||||||||||||||||||||||||||||||||||||||||  ||||||||  ||||||||
248  ATGTCTGGCTGACCCAGGAGTGGGAAGATTACCGCCTCACATGGAAGCCT  297

301  GAAGAGTTTGACAACATGAAGAAAGTTCGGCTCCCTTCCAAACACATCTG  350
     ||  ||  ||  |||||  ||||||||||  |||||||||||||||||||||||
     ||  ||  ||  |||||  ||||||||||  |||||||||||||||||||||||
248  GAGGACTTCGACAATATGAAGAAAGTCCGGCTCCCTTCCAAACACATCTG  347
```

FIG. 9A

```
351  GCTCCCAGATGTGGTCCTGTACAACAATGCTGACGGCATGTACGAGGTGT  400
     ||||||||||||||  ||||||||||||||||||||||||||||  |
     ||||||||||||||  ||||||||||||||||||||||||||||  |
348  GCTCCCAGATGTGGTTCTATACAACAATGCTGACGGCATGTACGAAGTCT  397

401  CCTTCTATTCCAATGCCGTGGTCTCCTATGATGGCAGCATCTTCTGGCTG  450
     ||||||||||||||| |||||||||||||||||||||||||||| |||||
     ||||||||||||||| |||||||||||||||||||||||||||| |||||
398  CCTTCTATTCCAATGCTGTGGTCTCCTATGATGGCAGCATCTTTTGGCTA  447

SphI
451  CCGCCTGCCATCTACAAGAGCGCATGCAAGATTGAAGTAAAGCACTTCCC  500
     || |||||||||||||||||| ||||||||||||| || ||||||||||
     || |||||||||||||||||| ||||||||||||| || ||||||||||
448  CCACCTGCCATCTACAAGAGTGCATGCAAGATTGAGGTGAAGCACTTCCC  497

501  ATTTGACCAGCAGAACTGCACCATGAAGTTCCGTTCGTGGACCTACGACC  550
     |||||||||||||| |||||||||||||||| || || |||||||||||
     |||||||||||||| |||||||||||||||| || || |||||||||||
498  ATTTGACCAGCAGAATTGCACCATGAAGTTTCGCTCATGGACCTACGACC  547

551  GCACAGAGATCGACTTGGTGCTGAAGAGTGAGGTGGCCAGCCTGGACGAC  600
     |  || ||||| ||| ||||||| || ||||| |||||||| ||||| |||
     |  || ||||| ||| ||||||| || ||||| |||||||| ||||| |||
548  GTACTGAGATTGACCTGGTGCTCAAAAGTGATGTGGCCAGTCTGGATGAC  597

601  TTCACACCTAGTGGTGAGTGGGACATCGTGGCGCTGCCGGGCCGCGGCAA  650
     |||||||| || || ||||||||||| | || |||||||||   ||||
     |||||||| || || ||||||||||| | || |||||||||   ||||
598  TTCACACCCAGCGGGGAGTGGGACATCATCGCACTGCCAGGCCGACGCAA  647

651  CGAGAACCCCGACGACTCTACGTACGTGGACATCACGTATGACTTCATCA  700
     ||||||||| |||||||| || || |||||||||| ||||||||||||||
     ||||||||| |||||||| || || |||||||||| ||||||||||||||
648  CGAGAACCCAGACGACTCCACCTATGTGGACATCACCTATGACTTCATCA  697
```

FIG. 9B

```
701  TTCGCCGCAAGCCGCTCTTCTACACCATCAACCTCATCATCCCTGTGTG  750
     ||||  ||||||  ||  ||||||||||||  ||||||||||||||||||  ||
     ||||  ||||||  ||  ||||||||||||  ||||||||||||||||||  ||
698  TTCGTCGCAAACCACTCTTCTACACTATCAACCTCATCATCCCTGCGTA  747

751  CTCATCACCTCGCTAGCCATCCTTGTCTTCTACCTGCCATCGACTGTGG  800
     |||||||||||||| ||||||||| |||||||||||||| || ||||||||
     |||||||||||||| ||||||||| |||||||||||||| || ||||||||
748  CTCATCACCTCGCTGGCCATCCTGGTCTTCTACCTGCCCTCAGACTGTGG  797

801  CGAGAAGATGACGTTGTGCATCTCAGTGCTGCTGGCGCTCACGGTCTTCC  850
     ||  ||||||||| | || || ||  |||||||| || |||||||| ||||
     ||  ||||||||| | || || ||  |||||||| || |||||||| ||||
798  TGAAAAGATGACACTTTGTATTTCTGTGCTGCTAGCACTCACGGTGTTCC  847

851  TGCTGCTCATCTCCAAGATCGTGCCTCCCACCTCCCTCGACGTGCCGCTC  900
     |||||||||||||||||||| |||||||||||||||||||||| || |||||
     |||||||||||||||||||| |||||||||||||||||||||| || |||||
848  TGCTGCTCATCTCCAAGATTGTGCCTCCCACCTCCCTCGATGTACCGCTG  897

901  GTCGGCAAGTACCTCATGTTCACCATGGTGCTTGTCACCTTCTCCATCGT  950
     || ||||||||||||||||| ||||||||||| |||||||||||||||||||
     || ||||||||||||||||| ||||||||||| |||||||||||||||||||
898  GTGGGCAAGTACCTCATGTTTACCATGGTGCTAGTCACCTTCTCCATCGT  947

951  CACCAGCGTGTGCGTGCTCAACGTGCACCACCGCTCGCCCACCACGCACA  1000
     |||||||||||| ||||||| ||||||||||||||||||  |||||||||||
     |||||||||||| ||||||| ||||||||||||||||||  |||||||||||
948  CACCAGCGTGTGTGTGCTCAATGTGCACCACCGCTCGCCTACCACGCACA  997

1001 CCATGGCGCCCTGGGTGAAGGTCGTCTTCCTGGAGAAGCTGCCCGCGCTG  1050
     |||||||  ||||||||  |||||  ||||||||||||||||||||||  |  |||
     |||||||  ||||||||  |||||  ||||||||||||||||||||||  |  |||
998  CCATGGCCCCCTGGGTCAAGGTGGTCTTCCTGGAGAAGCTGCCCACCCTG  1047
```

FIG. 9C

```
1051 CTCTTCATGCAGCAGCCACGCCATCATTGCGCCCGTCAGCGCCTGCGCCT 1100
     ||||||  ||||||||||||||||| |  || ||  |||||||| ||||||  |
     ||||||  ||||||||||||||||| |  || ||  |||||||| ||||||  |
1048 CTCTTCCTGCAGCAGCCACGCCACCGCTGTGCACGTCAGCGTCTGCGCTT 1097

1101 GCGGCGACGCCAGCGTGAGCGCGAGGGCGCTGGAGCCCTCTTCTTCCGCG 1150
     | || | ||||||||| ||||| ||||||    |  || | |||||||| |
     | || | ||||||||| ||||| ||||||    |  || | |||||||| |
1098 GAGGAGGCGCCAGCGAGAGCGTGAGGGC...GAGGCGGTTTTCTTCCGTG 1144

1151 AAGCCCCAGGGGCCGACTCCTGCACGTGCTTCGTCAACCGCGCGTCGGTG 1200
     |||  || |  ||| |||  |  || || ||||| |||||||  || || |||
     |||  || |  ||| |||  |  || || ||||| |||||||  || || |||
1145 AAGGTCCTGCGGCTGACCCATGTACCTGCTTTGTCAACCCTGCATCAGTG 1194

1201 CAGGGGTTGGCCGGGGCCTTCGGGGCTGAGCCTGCACCAGTGGCGGGCCC 1250
     ||||| ||||| ||||| ||| | |||||||||  |  ||   || ||||||
     ||||| ||||| ||||| ||| | |||||||||  |  ||      || |||||
1195 CAGGGCTTGGCTGGGGCTTTCCGAGCTGAGCCCACTGCA...GCCGGCCC 1241

1251 CGGGCGCTCAGGGGAGCCGTGTGGCTGTGGCCTCCGGGAGGCGGTGGACG 1300
     ||||||||  |  || |||  ||  |||||||||||||||| || |||||| |
     ||||||||  |  || |||  ||  |||||||||||||||| || |||||| |
1242 GGGGCGCTCTGTGGGGCCATGCAGCTGTGGCCTCCGGGAAGCAGTGGATG 1291

1301 GCGTGCGCTTCATCGCAGACCACATGCGGAGCGAGGACGATGACCAGAGC 1350
     ||||  ||||||||| ||  |||||||||| ||  |||||||  |||||||||||
     ||||  ||||||||| ||  |||||||||| ||  |||||||  |||||||||||
1292 GCGTACGCTTCATTGCGGACCACATGCGAAGTGAGGATGATGACCAGAGT 1341

1351 GTGAGTGAGGACTGGAAGTACGTCGCCATGGTGATCGACCGCCTCTTCCT 1400
     ||||| ||||||||||| |||||  |||||||||||||||||||||||  |||||
     ||||| ||||||||||| |||||  |||||||||||||||||||||||  |||||
1342 GTGAGGGAGGACTGGAAATACGTTGCCATGGTGATCGACCGCCTGTTCCT 1391
```

FIG. 9D

```
                                                   .               .                .                 .       PstI
1401  CTGGATCTTTGTCTTTGTCTGTGTCTTTGGCACCATCGGCATGTTCCTGC  1450
      ||||||||||||||||||||||||||||||  |||  |||||||||||||||
      ||||||||||||||||||||||||||||||  |||  |||||||||||||||
1392  GTGGATCTTTGTCTTTGTCTGTGTCTTTGGGACCGTCGGCATGTTCCTGC  1441

.                 .                 .                 .                 .
1451  AGCCTCTCTTCCAGAACTACACCACCACCACCTTCCTCCACTCAGACCAC  1500
      ||||||||||||||||||||||||    ||||  ||||||||||| | ||||||
      ||||||||||||||||||||||||    ||||  ||||||||||| | ||||||
1442  AGCCTCTCTTCCAGAACTACACTGCCACTACCTTCCTCCACCCTGACCAC  1491

.                  .
1501  TCAGCCCCCAGCTCCAAGTGA  1521
      |||||  ||||||||||||||
      |||||  ||||||||||||||
1492  TCAGCTCCCAGCTCCAAGTGA  1512
```

FIG. 9E

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 195 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: misc_feature
      (B) LOCATION: 1..195
      (D) OTHER INFORMATION: /note= "Human neuronal NAChR
          alpha-2 cDNA shown as top sequence of Fig 7A."

(xi) SEQUENCE DESCRIPTION: SEQ ID NO:1:

```
GCTAAACAGG AGTGGAGCGA CTACAAACTG CGCTGGAACC CCGCTGATTT TGGCAACATC      60

ACATCTCTCA GGGTCCCTTC TGAGATGATC TGGATCCCCG ACATTGTTCT CTACAACAAA     120

AATGGGGAGT TTGCAGTGAC CCACATGACC AAGGCCCACC TCTTCTCCAC GGGCACTGTG     180

CACTGGGTGC CCCCC                                                      195
```

(2) INFORMATION FOR SEQ ID NO:2:

(i) SEQUENCE CHARACTERISTICS:
      (A) LENGTH: 209 base pairs
      (B) TYPE: nucleic acid
      (C) STRANDEDNESS: both
      (D) TOPOLOGY: both -continued (ii) MOLECULE TYPE: cDNA (ix) FEATURE:
        (A) NAME/KEY: misc_feature
        (B) LOCATION: 1..209
        (D) OTHER INFORMATION: /note= "Rat neuronal NAChR alpha-2
            cDNA shown as the bottom nucleotide sequence in
            Figure 7A."

(xi) SEQUENCE DESCRIPTION: SEQ ID NO:2:

```
CCAATGTCTG GCTAAAGCAG GAATGGAATG ACTACAAGCT GCGCTGGGAC CCGGCTGAGT      60

TTGGCAATGT CACCTCCCTG CGCGTCCCTT CAGAGATGAT CTGGATCCCA GACATTGTCC     120

TCTACAACAA TGCAGATGGG GAGTTTGCGG TGACCCACAT GACCAAGGCT CACCTCTTCT     180

TCACGGGCAC TGTGCACTGG GTGCCCCCA                                      209
```

(2) INFORMATION FOR SEQ ID NO:3:

(i) SEQUENCE CHARACTERISTICS:
        (A) LENGTH: 202 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..202
        (D) OTHER INFORMATION: /note= "Human neuronal NAChR
            alpha-2 cDNA shown as top sequence in Fig 7B."

(xi) SEQUENCE DESCRIPTION: SEQ ID NO:3:

```
CCCCTTCGAC CAGCAGAACT GCAAGATGAA GTTTGGCTCC TGGACTTATG ACAAGGCCAA      60

GATCGACCTG GAGCAGATGG AGCAGACTGT GGACCTGAAG GACTACTGGG AGAGCGGCGA     120

GTGGGCCATC GTCAATGCCA CGGGCACCTA CAACAGCAAG AAGTACGACT GCTGCGCCGA     180

GATCTACCCC GACGTCACCT AG                                             202
```

(2) INFORMATION FOR SEQ ID NO:4:

(i) SEQUENCE CHARACTERISTICS:
        (A) LENGTH: 250 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..250
        (D) OTHER INFORMATION: /note= "Rat neuronal NAChR alpha-2
            cDNA shown as bottom sequence in Fig 7B."

(xi) SEQUENCE DESCRIPTION: SEQ ID NO:4:

```
CCCCTTCGAC CAGCAGAACT GCAAGATGAA GTTTGGCTCC TGGACATATG ACAAGGCCAA      60

GATCGATCTG GAGCAGATGG AGAGGACAGT GGACCTGAAG GACTACTGGG AGAGTGGCGA     120

GTGGGCCATT ATCAATGCCA CCGGAACCTA TAACAGTAAG AAGTACGACT GCTGCGCGGA     180

GATCTACCCC GATGTCACCT ACTACTTTGT GATCCGGCGG CTGCCGCTGT TCTATACCAT     240

CAACCTCATC                                                           250
```

(2) INFORMATION FOR SEQ ID NO:5:

(i) SEQUENCE CHARACTERISTICS:
        (A) LENGTH: 278 base pairs (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..278
        (D) OTHER INFORMATION: /note= "Human neuronal NAChR
            alpha-3 cDNA shown as top sequence in Fig 8A."

(xi) SEQUENCE DESCRIPTION: SEQ ID NO:5:

CTGGCAGCAG AGGCTGAGCA CCGTCTATTT GAGCGGCTGT TTGAAGATTA CAATGAGATC      60

ATCCGGCCTG TAGCCAACGT GTCTGACCCA GTCATCATCC ATTTCGAGGT GTCCATGTCT     120

CAGCTGGTGA AGGTGGATGA AGTAAACCAG ATCATGGAGA CCAACCTGTG GCTCAAGCAA     180

ATCTGGAATG ACTACAAGCT GAAGTGGAAC CCCTCTGACT ATGGTGGGGC AGAGTTCATG     240

CGTGTCCCTG CACAGAAGAT CTGGAAGCCA GACATTGT                             278

(2) INFORMATION FOR SEQ ID NO:6:

(i) SEQUENCE CHARACTERISTICS:
        (A) LENGTH: 300 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..300
        (D) OTHER INFORMATION: /note= "Rat neuronal NAChR alpha-3
            cDNA shown as bottom sequence of Fig 8A."

(xi) SEQUENCE DESCRIPTION: SEQ ID NO:6:

GATGCTGCTG CCAGCGGCCA GTGCCTCAGA AGCTGAGCAC CGCCTGTTCC AGTACCTGTT      60

CGAAGATTAC AACGAGATCA TCCGGCCAGT GGCTAATGTG TCCCATCCAG TCATCATCCA     120

GTTTGAGGTG TCCATGTCTC AGCTGGTGAA GGTGGATGAA GTAAACCAGA TCATGGAAAC     180

CAACCTGTGG CTGAAGCAAA TCTGGAATGA CTACAAGCTG AAATGGAAAC CCTCTGACTA     240

CCAAGGGGTG GAGTTCATGC GTGTTCCTGC AGAGAAGATC TGGAAACCAG ACATCGTACT     300

(2) INFORMATION FOR SEQ ID NO:7:

(i) SEQUENCE CHARACTERISTICS:
        (A) LENGTH: 305 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..305
        (D) OTHER INFORMATION: /note= "Human neuronal NAChR
            alpha-3 cDNA shown as top sequence in Fig 8B."

(xi) SEQUENCE DESCRIPTION: SEQ ID NO:7:

TTCCAGGTGG ACGACAAGAC CAAAGCCTTA CTCAAGTACA CTGGGGACGT GACTTGGATA      60

CCTCCGGCCA TCTTTAAGAG CTCCTGTAAA ATCGACGTGA CCTACTTCCC GTTTGATTAC     120

CAAAACTGTA CCATGAAGTT CGGTTCCTGG TCCTACGATA AGGCGAAAAT CGATCTGGTC     180

CTGATCGGCT CTTCCATGAA CCTCAAGGAC TATTGGGAGA GCGGCGAGTG GGCCATCATC     240

```
AAAGCCCCAG GCTACAAACA CGACATCAAG TACAACTGCT GCGAGGAGAT CTACCCCGAC    300

ATCAC                                                                305
```

(2) INFORMATION FOR SEQ ID NO:8:

(i) SEQUENCE CHARACTERISTICS:
        (A) LENGTH: 350 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..350
        (D) OTHER INFORMATION: /note= "Rat neuronal NAChR alpha-3
            cDNA shown as bottom sequence in Fig 8B."

(xi) SEQUENCE DESCRIPTION: SEQ ID NO:8:

```
GTACAACAAC GCTGATGGGG ATTTCCAGGT GGATGACAAG ACCAAAGCTC TACTCAAGTA     60

CACAGGAGAA GTGACTTGGA TCCCGCCGGC CATCTTTAAG AGCTCATGCA AAATCGACGT    120

GACCTACTTC CCATTCGACT ACCAAAACTG CACCATGAAG TTCGGCTCCT GGTCCTACGA    180

CAAGGCAAAG ATCGACCTGG TCCTCATCGG CTCCTCCATG AACCTCAAGG ACTACTGGGA    240

GAGTGGCGAG TGGGCTATCA TTAAAGCCCC GGGCTACAAA CATGAAATCA AGTACAACTG    300

CTGTGAGGAG ATCTACCAAG ACATCACGTA CTCGCTGTAC ATCCGTCGCC                350
```

(2) INFORMATION FOR SEQ ID NO:9:

(i) SEQUENCE CHARACTERISTICS:
        (A) LENGTH: 1521 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..1521
        (D) OTHER INFORMATION: /note= "Human neuronal NAChR beta-2
            cDNA shown as top sequence in Fig 9."

(xi) SEQUENCE DESCRIPTION: SEQ ID NO:9:

```
ATGCCCGCTG GCATGGCCCG GCGCTGCGGC CCCGTGGCGC TGCTCCTTGG CTTCGGCCTC     60

CTCCGGCTGT GCTCAGGGGT GTGGGGTACG GATACAGAGG AGCGGCTGGT GGAGCATCTC    120

CTGGATCCTT CCCGCTACAA CAAGCTTATC CGCCCAGCCA CCAATGGCTC TGAGCTGGTG    180

ACAGTACAGC TTATGGTGTC ACTGGCCCAG CTCATCAGTG TGCATGAGCG GGAGCAGATC    240

ATGACCACCA ATGTCTGGCT GACCCAGGAG TGGGAAGATT ATCGCCTCAC CTGGAAGCCT    300

GAAGAGTTTG ACAACATGAA GAAAGTTCGG CTCCCTTCCA AACACATCTG GCTCCCAGAT    360

GTGGTCCTGT ACAACAATGC TGACGGCATG TACGAGGTGT CCTTCTATTC CAATGCCGTG    420

GTCTCCTATG ATGGCAGCAT CTTCTGGCTG CCGCCTGCCA TCTACAAGAG CGCATGCAAG    480

ATTGAAGTAA AGCACTTCCC ATTTGACCAG CAGAACTGCA CCATGAAGTT CCGTTCGTGG    540

ACCTACGACC GCACAGAGAT CGACTTGGTG CTGAAGAGTG AGGTGGCCAG CCTGGACGAC    600

TTCACACCTA GTGGTGAGTG GGACATCGTG GCGCTGCCGG GCCGCGGCAA CGAGAACCCC    660

GACGACTCTA CGTACGTGGA CATCACGTAT GACTTCATCA TTCGCCGCAA GCCGCTCTTC    720

TACACCATCA ACCTCATCAT CCCCTGTGTG CTCATCACCT CGCTAGCCAT CCTTGTCTTC    780
```

| TACCTGCCAT CCGACTGTGG CGAGAAGATG ACGTTGTGCA TCTCAGTGCT GCTGGCGCTC | 840 |
| ACGGTCTTCC TGCTGCTCAT CTCCAAGATC GTGCCTCCCA CCTCCCTCGA CGTGCCGCTC | 900 |
| GTCGGCAAGT ACCTCATGTT CACCATGGTG CTTGTCACCT TCTCCATCGT CACCAGCGTG | 960 |
| TGCGTGCTCA ACGTGCACCA CCGCTCGCCC ACCACGCACA CCATGGCGCC CTGGGTGAAG | 1020 |
| GTCGTCTTCC TGGAGAAGCT GCCCGCGCTG CTCTTCATGC AGCAGCCACG CCATCATTGC | 1080 |
| GCCCGTCAGC GCCTGCGCCT GCGGCGACGC CAGCGTGAGC GCGAGGGCGC TGGAGCCCTC | 1140 |
| TTCTTCCGCG AAGCCCCAGG GGCCGACTCC TGCACGTGCT TCGTCAACCG CGCGTCGGTG | 1200 |
| CAGGGGTTGG CCGGGGCCTT CGGGGCTGAG CCTGCACCAG TGGCGGGCCC CGGGCGCTCA | 1260 |
| GGGGAGCCGT GTGGCTGTGG CCTCCGGGAG GCGGTGGACG GCGTGCGCTT CATCGCAGAC | 1320 |
| CACATGCGGA GCGAGGACGA TGACCAGAGC GTGAGTGAGG ACTGGAAGTA CGTCGCCATG | 1380 |
| GTGATCGACC GCCTCTTCCT CTGGATCTTT GTCTTTGTCT GTGTCTTTGG CACCATCGGC | 1440 |
| ATGTTCCTGC AGCCTCTCTT CCAGAACTAC ACCACCACCA CCTTCCTCCA CTCAGACCAC | 1500 |
| TCAGCCCCCA GCTCCAAGTG A | 1521 |

(2) INFORMATION FOR SEQ ID NO:10:

(i) SEQUENCE CHARACTERISTICS:
        (A) LENGTH: 1512 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..1512
        (D) OTHER INFORMATION: /note= "Rat neuronal NAChR beta-2
            cDNA shown as bottom nucleotide sequence in Figure
            9."

(xi) SEQUENCE DESCRIPTION: SEQ ID NO:10:

| ATGCTGGCTT GCATGGCCGG GCACTCCAAC TCAATGGCGC TGTTCAGCTT CAGCCTTCTT | 60 |
| TGGCTGTGCT CAGGGGTTTT GGGAACTGAC ACAGAGGAGC GGCTAGTGGA GCATCTCTTA | 120 |
| GATCCCTCCC GCTATAACAA GCTGATTCGT CCAGCTACTA ACGGCTCTGA GCTGGTGACT | 180 |
| GTACAGCTCA TGGTATCATT GGCTCAGCTC ATTAGTGTGC ACGAGCGGGA GCAGATCATG | 240 |
| ACCACCAATG TCTGGCTGAC CCAGGAGTGG GAAGATTACC GCCTCACATG GAAGCCTGAG | 300 |
| GACTTCGACA ATATGAAGAA AGTCCGGCTC CCTTCCAAAC ACATCTGGCT CCCAGATGTG | 360 |
| GTTCTATACA ACAATGCTGA CGGCATGTAC GAAGTCTCCT TCTATTCCAA TGCTGTGGTC | 420 |
| TCCTATGATG GCAGCATCTT TTGGCTACCA CCTGCCATCT ACAAGAGTGC ATGCAAGATT | 480 |
| GAGGTGAAGC ACTTCCCATT TGACCAGCAG AATTGCACCA TGAAGTTTCG CTCATGGACC | 540 |
| TACGACCGTA CTGAGATTGA CCTGGTGCTC AAAAGTGATG TGGCCAGTCT GGATGACTTC | 600 |
| ACACCCAGCG GGGAGTGGGA CATCATCGCA CTGCCAGGCC GACGCAACGA GAACCCAGAC | 660 |
| GACTCCACCT ATGTGGACAT CACCTATGAC TTCATCATTC GTCGCAAACC ACTCTTCTAC | 720 |
| ACTATCAACC TCATCATCCC CTGCGTACTC ATCACCTCGC TGGCCATCCT GGTCTTCTAC | 780 |
| CTGCCCTCAG ACTGTGGTGA AAAGATGACA CTTTGTATTT CTGTGCTGCT AGCACTCACG | 840 |
| GTGTTCCTGC TGCTCATCTC CAAGATTGTG CCTCCCACCT CCCTCGATGT ACCGCTGGTG | 900 |
| GGCAAGTACC TCATGTTTAC CATGGTGCTA GTCACCTTCT CCATCGTCAC CAGCGTGTGT | 960 |
| GTGCTCAATG TGCACCACCG CTCGCCTACC ACGCACACCA TGGCCCCCTG GGTCAAGGTG | 1020 |

```
GTCTTCCTGG AGAAGCTGCC CACCCTGCTC TTCCTGCAGC AGCCACGCCA CCGCTGTGCA    1080

CGTCAGCGTC TGCGCTTGAG GAGGCGCCAG CGAGAGCGTG AGGGCGAGGC GGTTTTCTTC    1140

CGTGAAGGTC CTGCGGCTGA CCCATGTACC TGCTTTGTCA ACCCTGCATC AGTGCAGGGC    1200

TTGGCTGGGG CTTTCCGAGC TGAGCCCACT GCAGCCGGCC CGGGGCGCTC TGTGGGGCCA    1260

TGCAGCTGTG GCCTCCGGGA AGCAGTGGAT GGCGTACGCT TCATTGCGGA CCACATGCGA    1320

AGTGAGGATG ATGACCAGAG TGTGAGGGAG GACTGGAAAT ACGTTGCCAT GGTGATCGAC    1380

CGCCTGTTCC TGTGGATCTT TGTCTTTGTC TGTGTCTTTG GGACCGTCGG CATGTTCCTG    1440

CAGCCTCTCT TCCAGAACTA CACTGCCACT ACCTTCCTCC ACCCTGACCA CTCAGCTCCC    1500

AGCTCCAAGT GA                                                        1512

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCTTTCGAT ATCAGAATTC G                                              21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGCTCGAATT CTGATATCGA A                                              21
```

HUMAN NEURONAL NICOTINIC ACETYLCHOLINE RECEPTOR COMPOSITIONS AND METHODS EMPLOYING SAME

The present application claims priority from International Application No. PCT/US91/02311, filed Apr. 3, 1991, which is a continuation-in-part of U.S. Ser. No. 07/504,455, filed Apr. 3, 1990, issued Nov. 29, 1994 as U.S. Pat. No. 5,369,028.

FIELD OF THE INVENTION

This invention relates to neuronal nicotinic acetylcholine receptor genes and proteins. In a particular aspect, the present invention relates to human neuronal nicotinic acetylcholine receptor genes and proteins. In a further aspect, the present invention relates to methods for determining the presence of neuronal nicotinic acetylcholine receptor activity in cells thought to have genes encoding such proteins. In yet another aspect, the present invention relates to methods for determining the agonist or antagonist activity of compounds which might interact with neuronal nicotinic acetylcholine receptors.

BACKGROUND OF THE INVENTION

Most theories on how the nervous system functions depend heavily on the existence and properties of cell to cell contacts known as synapses. For this reason, the study of synapses has been a focal point for neuroscience research for many decades.

Because of its accessibility to biochemical and electrophysiological techniques, and because of its elegant, well defined structure, the neuromuscular synapse (also known as the neuromuscular junction), which occurs at the point of nerve to muscle contact, is one of the most studied and best understood synapses. At the neuromuscular junction, the nerve cell releases a chemical neurotransmitter, acetylcholine, which binds to nicotinic acetylcholine receptor proteins located on post-synaptic muscle cells. The binding of acetylcholine results in a conformational change in the nicotinic acetylcholine receptor protein. This change is manifested by the opening of a transmembrane channel in the receptor which is permeable to cations. The resulting influx of cations depolarizes the muscle and ultimately leads to muscle contraction.

Biological and structural studies have shown that the nicotinic acetylcholine receptor in muscle is a glycoprotein composed of five subunits with the stoichiometry $\alpha\alpha\beta\gamma\Delta$ (alpha-alpha-beta-gamma-delta). From these same studies, it is known that each of the subunits has a mass of about 50–60 kilodaltons and is encoded by a separate gene. In vitro reconstitution experiments have shown that this $\alpha\alpha\beta\gamma\Delta$ complex is a functional receptor containing both ligand binding sites and a ligand-gated transmembrane channel.

It is now known that a variety of neurotransmitters and neurotransmitter receptors exist in the central and peripheral nervous systems. Despite this knowledge, there is still little understanding of the diversity of receptors for a particular neurotransmitter, or of how this diversity might generate different responses to a given neurotransmitter, or to other modulating ligands, in different regions of the brain. On a larger scale, there is little appreciation of how the use of a particular synapse makes it more or less efficient, or hnges in neuronal circuits might be accomplished by the modification of synapses.

An understanding of the molecular mechanisms involved in neurotransmission in the central nervous system is limited by the complexity of the system. The cells are small, have extensive processes, and often have thousands of synapses deriving from inputs from many different parts of the brain. In addition, the actual number of neurotransmitter receptors is low, making their purification difficult, even under the best of circumstances. Consequently, neither cellular nor biochemical approaches to studying neurotransmission in the central nervous system has been particularly fruitful. This is unfortunate because it is quite probable that the treatment of dementia, Alzheimer's disease and other forms of mental illness will involve modification of synaptic transmission with specific drugs.

Nicotinic acetylcholine receptors found at the vertebrate neuromuscular junction, in vertebrate sympathetic ganglia and in the vertebrate central nervous system can be distinguished pharmacologically on the basis of ligands that open or block the ion channel. For example, the elapid $\alpha$-neurotoxins that block activation of nicotinic acetylcholine receptors at the neuromuscular junction do not block activation of neuronal nicotinic acetylcholine receptors found on several different cell lines.

To gain access to the neuronal acetylcholine receptors, traditional biochemical and neurophysiological methods have been abandoned in favor of the newer methods of molecular biology. More specifically, using molecular cloning techniques, complementary DNA clones were isolated which encode the acetylcholine receptor expressed in the Torpedo fish electric organ, a highly enriched source of receptor. The cDNA clones isolated from the fish electric organ were then used in nucleic acid hybridization experiments to obtain cDNA and genomic clones for the subunits of the acetylcholine receptor expressed in mouse skeletal muscle.

The availability of cDNA clones encoding muscle nicotinic receptors made it possible to extend these studies in the important direction of neuronal receptors. More specifically, based on the assumption that neuronal nicotinic receptors are evolutionarily related to muscle receptors, and that this relationship will be reflected at the genetic level by nucleotide sequence homology, the cDNA clones encoding the muscle nicotinic receptor were used to screen rat cDNA and genomic libraries for related neuronal mRNAs or genes. This method has resulted in the isolation of several neuronal cDNA clones that have significant sequence homology with the muscle acetylcholine clones.

That the neuronal nicotinic acetylcholine receptors differ from muscle nicotinic acetylcholine receptors is evidenced by the fact that neuronal receptors can be constituted from only two different gene-products (i.e., one alpha subunit and one beta subunit). This is significant since, in all experiments reported to date, muscle nicotinic acetylcholine receptors have been formed with $\alpha\beta\delta\Delta$ subunits, $\alpha\beta\Delta$ subunits, $\alpha\beta\delta$ subunits or $\alpha\delta\Delta$ subunits, but not with any pairwise combinations. See Kurosaki et al., *FEBS Letters* 214, 253–258 (1987).

In order to further extend such studies, to provide proteins useful for assaying compounds as potential agonists or antagonists for human neuronal nicotinic acetylcholine receptors, as well as cell lines capable of expressing such proteins, we undertook to isolate and characterize clones which encode various subunits of the human neuronal nicotinic acetylcholine receptor; we further undertook to develop methods for expressing cloned human neuronal nicotinic acetylcholine receptor sequences in recombinant cell lines; and we further undertook to develop assays for identifying which of the resultant recombinant cell lines express functional neuronal nicotinic receptors.

SUMMARY OF THE INVENTION

In accordance with the present invention, we have isolated and characterized clones which encode the alpha2, alpha3 and beta2 subunits of the human neuronal nicotinic acetylcholine receptor.

The neuronal clones of the present invention encode a family of acetylcholine receptors having unique pharmacological properties. The demonstration that the nicotinic acetylcholine receptors are much more diverse than previously expected offers an opportunity for a high level of pharmaceutical intervention and a chance to design new drugs that affect specific receptor subunits. Such subtypes make it possible to observe the effect of a drug substance on a particular receptor subtype, which can be expressed in a recombinant cell in the absence of the other receptor subtypes. Information derived from these observations will allow the development of new drugs that are more specific, and therefore have fewer unwanted side effects.

In addition, the availability of human neuronal receptors makes it possible to perform initial in vitro screening of the drug substance in a test system which is specific for humans. While it is true that the drug eventually has to be administered directly to the human patient, it is probable that useful drugs are being missed because conventional drug screening is limited to assays employing non-human receptors, human tissue preparations (which are likely to be contaminated with other receptors, both nicotinic and non-nicotinic in origin), and other suboptimal assay systems. Consequently, the ability to screen drug substances in vitro on specific receptor subtype(s) is likely to be more informative than merely screening the drug substance employing presently available suboptimal assay systems.

Both the receptor subunit genes and proteins of the present invention can be used for drug design and screening. For example, the cDNA clones encoding the human alpha2, alpha3 and beta2 receptor subunits can be transcribed in vitro to produce mRNA. This mRNA, either from a single subunit clone or from a combination of clones, can then be injected into oocytes where the mRNA directs the synthesis of the human receptor molecule(s). The resulting receptor-expressing oocytes can then be contacted with a test compound, and the agonist or antagonist effect thereof can then be evaluated by comparing oocyte response relative to positive and negative control compounds and positive and negative control oocytes. Alternatively, the clones may be placed downstream from appropriate gene regulatory elements and inserted into the genome of eukaryotic cells. This will result in transformed cell lines expressing a specific human receptor subtype, or specific combinations of subtypes. The derived cell lines can then be produced in quantity for similar reproducible quantitative analysis of the effects of drugs on receptor function.

BRIEF DESCRIPTION OF THE FIGURES

FIG. 7 is a comparison of about 500 base pairs of human alpha2 sequence with the corresponding rat sequence.

FIG. 8 is a comparison of about 650 base pairs of human alpha3 sequence with the corresponding rat sequence.

FIG. 9 is a comparison of the nucleotide sequence for the human and rat beta2 subunits.

DETAILED DESCRIPTION OF THE INVENTION

Figure 1:
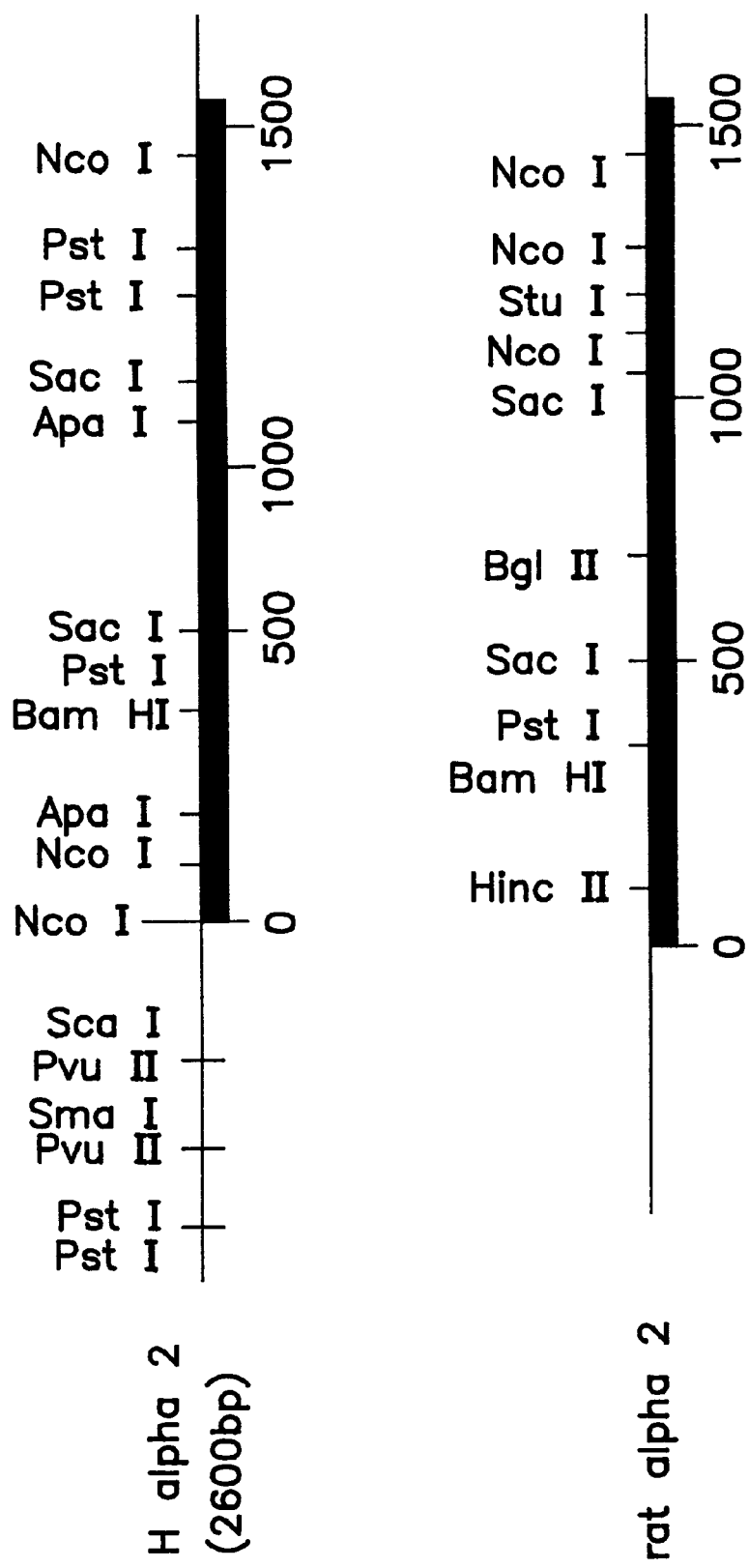
FIG. 1 is a restriction map of the alpha2 subunit gene of the human neuronal nicotinic acetylcholine receptor, compared to the corresponding rat gene.

In accordance with the present invention, there are provided substantially pure DNA sequence(s) encoding alpha subunit(s) of the human neuronal nicotinic acetylcholine receptor and/or substantially pure DNA sequence(s) encoding beta subunit(s) of the human neuronal nicotinic acetylcholine receptor.

In accordance with a particular embodiment of the present invention, there are provided mRNA sequences and polypeptides encoded by the above-described DNA sequences.

In accordance with yet another embodiment of the present invention, there are provided cells transformed with one or more of the above-described DNA sequences.

In accordance with still another embodiment of the present invention, there are provided substantially pure human neuronal acetylcholine receptors comprising at least one human alpha receptor subunit and at least one human beta subunit.

In accordance with a further embodiment of the present invention, there are provided methods for measuring the agonist or antagonist activity of test compounds (with respect to human neuronal acetylcholine receptors or subunits thereof), by measuring the response of the above-described cells and/or receptors, relative to the response of a control, when contacted with said compound.

In accordance with the latter embodiment of the present invention, the response of the above-described cells and/or receptors is determined by such assays as:

nicotine binding, $^{86}$Rb ion-flux, the electrophysiological response of said cells, or the electrophysiological response of oocytes transfected with RNA from said cells.

In accordance with yet another embodiment of the present invention, there is provided a method for assaying cells for the presence of neuronal nicotinic acetylcholine receptor activity. This is accomplished by determining the effect of known neuronal nicotinic acetylcholine agonists and/or antagonists on the influx of $^{86}$Rb ions into cells, relative to the rate of influx of $^{86}$Rb ions into control cells.

In accordance with a further embodiment of the present invention, there is provided an alternative method for assaying cells for the presence of neuronal nicotinic acetylcholine receptor activity, employing a multi-step screening protocol comprising the steps:

(a) analyzing said cells for the presence of alpha and beta subunit RNAs, (b) analyzing those cells which are positive for the presence of alpha and beta subunit RNAs for their ability to bind nicotine or a nicotine agonists, relative to the nicotine binding ability of control cells known to express neuronal nicotinic acetylcholine receptors, and (b) determining the effect of known neuronal nicotinic acetylcholine agonists and/or antagonists on cells having the ability to bind nicotine or nicotine agonist on the influx of $^{86}Rb$ ions into said cells, relative to the rate of influx of $^{86}Rb$ ions into control cells.

In accordance with a still further embodiment of the present invention, there is provided a method for making cells having neuronal nicotinic acetylcholine receptor activity, employing a multi-step protocol comprising the steps:

(a) transfecting host cells with DNA encoding at least one alpha subunit of the neuronal nicotinic acetylcholine receptor and at least one beta subunit of the neuronal nicotinic acetylcholine receptor, then (b) analyzing said transfected cells for the presence of alpha and beta subunit RNAs, employing methods such as Northern blot or slot blot analysis, then (c) analyzing those cells which are positive for the presence of alpha and beta subunit RNAs for their ability to bind nicotine or a nicotine agonist, relative to the nicotine binding ability of control cells known to express neuronal nicotinic acetylcholine receptors, and (d) determining the effect of known neuronal nicotinic acetylcholine agonists and/or antagonists on cells having the ability to bind nicotine or a nicotine agonist on the influx of $^{86}Rb$ ions into control cells.

In accordance with the preceding two embodiments of the present invention, mRNA from cells which are positive for alpha and beta neuronal nicotinic acetylcholine subunits is injected into oocytes, which are then assayed for the presence of functional neuronal nicotinic acetylcholine receptors.

As used herein, the term agonist refers to a substance that activates receptor function; and the term antagonist refers to a substance that interferes with receptor function. Antagonists are of two types: competitive and non-competitive. A competitive antagonist (or competitive blocker) competes with the neurotransmitter for the same binding site. A non-competitive antagonist or blocker inactivates the functioning of the receptor by binding to a site other than the acetylcholine binding site.

As used herein, alpha2 refers to a gene, which has been identified in chick and rat, that encodes a neuronal subunit of the same name. DNA coding for the human neuronal alpha2 subunit has been deposited with the ATCC; the DNA (designated as HnAChRα2; a restriction map of which is shown in FIG. 1; and a partial nucleotide sequence of which is shown in FIG. 7) has been accorded ATCC Accession No. 68277.

Figure 2:
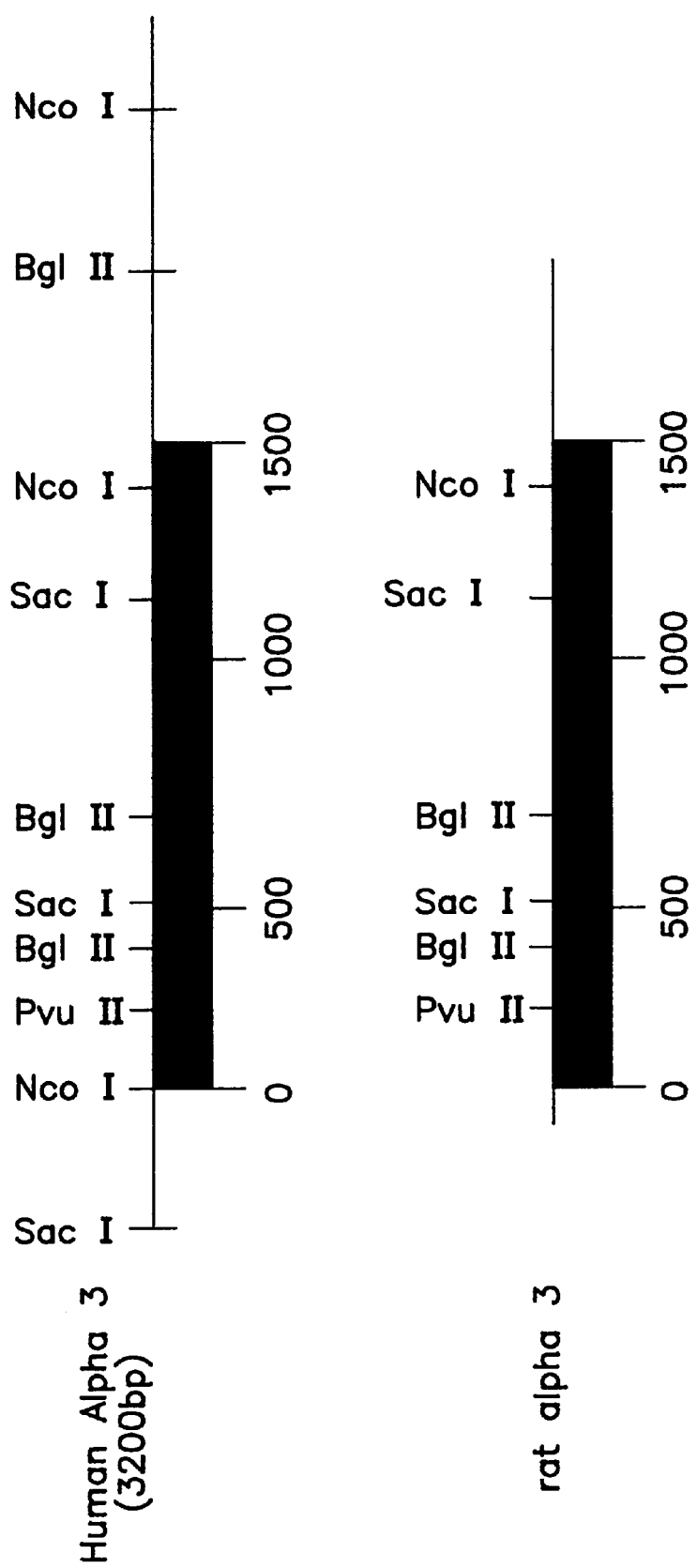
FIG. 2 is a restriction map of the alpha3 subunit gene of the human neuronal nicotinic acetylcholine receptor, compared to the corresponding rat gene.

As used herein, alpha3 refers to a gene that encodes a neuronal subunit of the same name. DNA coding for the human neuronal alpha3 subunit has been deposited with the ATCC; the DNA (designated as HnAChRα3; a restriction map of which is shown in FIG. 2; and a partial nucleotide sequence of which is shown in FIG. 8) has been accorded ATCC Accession No. 68278.

Figure 3:
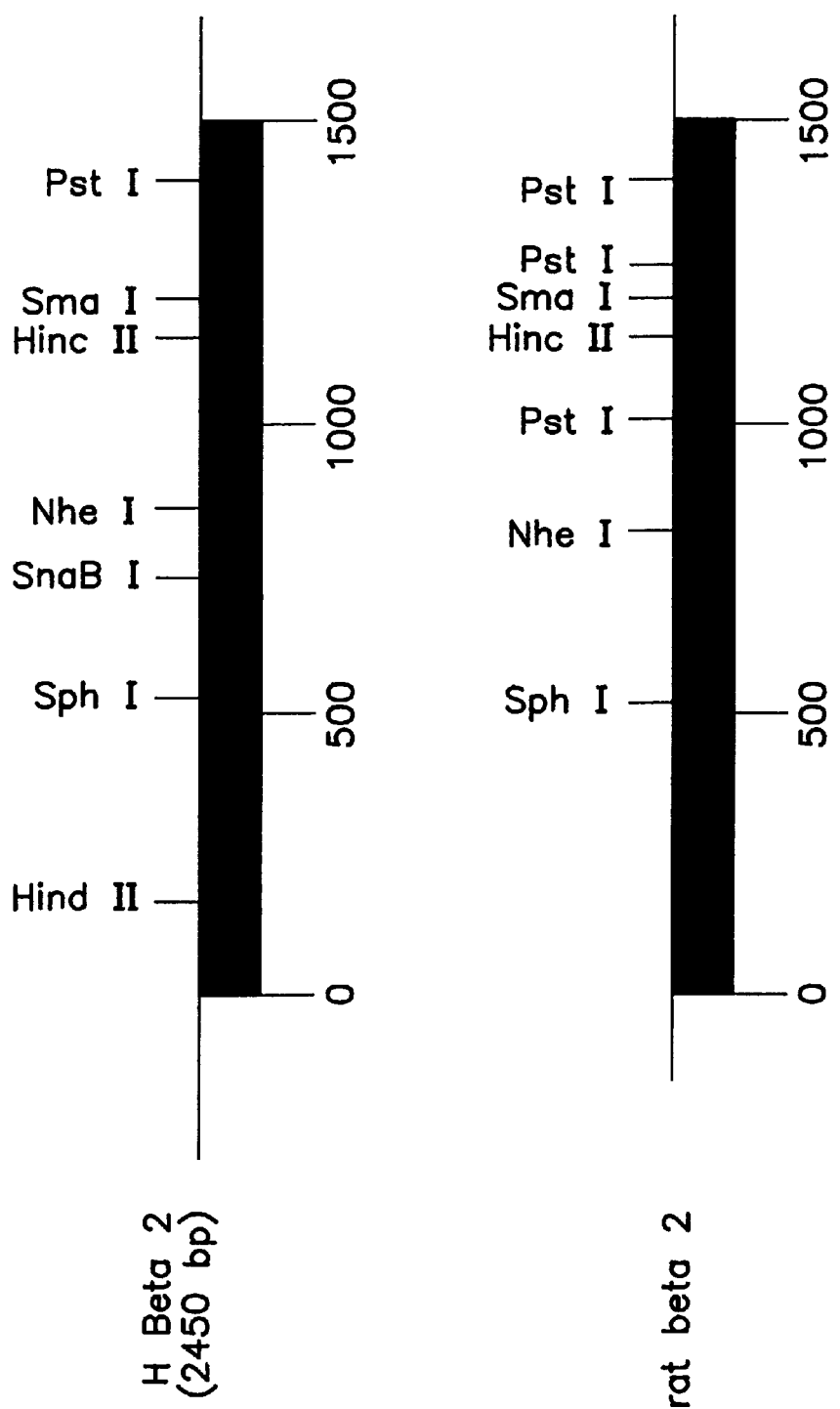
FIG. 3 is a restriction map of the beta2 subunit gene of the human neuronal nicotinic acetylcholine receptor, compared to the rat gene.

As used herein, beta2 refers to a gene encoding a neuronal nicotinic acetylcholine subunit of the same name. DNA coding for the human neuronal beta2 subunit has been deposited with the ATCC; the DNA (designated as HnAChRβ2; a restriction map of which is shown in FIG. 3; and the nucleotide sequence of which is shown in FIG. 9) has been accorded ATCC Accession No. 68279.

cDNA clones comprising human neuronal nicotinic acetylcholine receptor genes alpha2 (clone HnAChRα2), alpha3 (clone HnAChRα3), and beta2 (clone HnAChRβ2), all of which are in *E. coli* HB101, have been deposited at the American Type Culture Collection, Rockville, Md., U.S.A. (ATCC) under the terms of the Budapest Treaty on the International Recognition of Deposits of Microorganisms for Purposes of Patent Procedure and the Regulations promulgated under this Treaty. Samples of the cloned genes are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

Use of the phrase "substantial sequence homology" in the present specification and claims means that DNA, RNA or amino acid sequences which have slight and non-consequential sequence variations form the actual sequences disclosed and claimed herein are considered to be equivalent to the sequences of the present invention, and as such are within the scope of the appended claims. In this regard, "slight and non-consequential sequence variations" mean that "homologous" sequences (i.e., the sequences that have substantial sequence homology with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Use of the phrase "substantially pure" in the present specification and claims as a modifier of DNA, RNA, polypeptides or proteins means that the DNA, RNA, polypeptides or proteins so designated have been separated form their in vivo cellular environments through the efforts of human beings; as a result of this separation, the substantially pure DNAs, RNAs, polypeptides and proteins are useful in ways that the non-separated, impure DNAs, RNAs, polypeptides or proteins are not.

The invention DNA sequences were isolated employing analogous rat neuronal acetylcholine receptor subunit DNA fragments as probes in various human cDNA libraries. Due to the very low concentration of various human neuronal subunits in their native state, the frequently very localized presence of some of the human neuronal subunits in various sources of tissue, the difficulty in obtaining human neuronal (brain) tissue with which to work, as well as the hight level of care necessary to ensure the presence of intact mRNA in the source human neuronal tissue, a significant problem to be solved in order to achieve the objects of the present invention was identifying and obtaining suitable source(s) of DNA to probe for the desired sequences. By probing numerous human cDNA libraries, e.g., pre-frontal cortex cDNA, parietal cDNA, temporal cortex cDNA, brain stem cDNA, basal ganglia cDNA, and spinal cord cDNA, various fragments of the human neuronal subunits were identified (see, for example, FIGS. 4, 5 and 6). After partial sequencing and restriction mapping of several such fragments, and comparison of such fragments to the analogous rat sequences, it was possible to identify composite DNA sequences for the human neuronal alpha2, alpha3 and beta2 subunits, as disclosed and claimed herein.

In addition to their use as coding sequences for the production of human neuronal subunits and synthetic human neuronal receptors, the invention sequences can also be used as probes for the identification of additional human neuronal sequences. This is done by probing various sources of human neuronal DNA with invention sequences, then selecting those sequences having a significant level of sequence homology with the probe employed.

Invention DNA sequences can be transformed into a variety of host cells. Eukaryotic cells such as yeast or mammalian cells are presently preferred. A variety of suitable host mammalian cells, having desirable growth and handling properties, are readily available to those of skill in the art. Especially preferred for such purpose are human, rat or mouse cells.

Similarly, a variety of suitable yeast cells are readily available to host cells for the invention sequences. Especially preferred are yeast selected from *Pichia pastoris, Saccharomyces cerevisiae, Candida tropicalis, Hansenula polymorpha*, and the like.

Alternatively, the invention DNA sequences can be transcribed into RNA, which can then be transfected into amphibian cells for translation into protein. Suitable amphibian cells include Xenopus oocytes.

Cells transformed with invention DNA (or RNA) can optionally be further transformed with a reporter gene expression construct, so as to provide a ready, indirect measure of the presence of functional human neuronal receptor in the transformed cell. Such a reporter gene expression construct comprises:

a transcriptional control element; wherein said transcription control element, in said cell, is responsive to an intracellular condition that occurs when the human neuronal nicotinic acetylcholine receptor interacts with a compound having agonist or antagonist activity with respect to said receptor, and a reporter gene encoding a transcription and/or translational product; wherein said product can be, directly or indirectly, readily measured; and wherein said gene is in operative association with said transcriptional control element.

Transcriptional control elements contemplated for use in this embodiment of the present invention include the c-fos promoter, the vasoactive intestinal peptide gene promoter, the somatostatin gene promoter, the proenkephalin gene promoter, the phosphoenolpyruvate carboxykinase gene promoter, the NGFI-A gene promoter, and the like.

Reporter genes contemplated for use in this embodiment of the present invention include the chloramphenicol transferase (CAT) gene, the gene product of which can be readily analyzed by a variety of methods known in the art. See, for example, Nielsen, et al., *Anal. Biochem.* 179, 19–23 (1989), luciferase and other enzyme detection systems such as alkaline phosphatase, β-galactosidase, and the like.

A particularly useful application of the invention sequences is the ability to prepare synthetic receptors and synthetic receptor subunits which are substantially free of contamination from other, potentially competing proteins. Thus, a cell transformed with the invention alpha2 and beta2 sequences could express a synthetic receptor consisting essentially of only the alpha2 and beta2 subunits. Such a synthetic receptor would be useful for a variety of applications, e.g., as part of an assay system free of the interferences frequently present in prior art assay systems employing non-human receptors or human tissue preparations.

Similarly, a synthetic receptor could be prepared by causing cells transformed with the invention alpha3 and beta2 sequences to express the corresponding proteins. The resulting synthetic receptor would consist essentially of only the alpha3 and beta2 subunits. Such a synthetic receptor would be useful for a variety of applications, e.g., as part of an assay system free of the interferences frequently present in prior art assay systems employing non-human receptors or human tissue preparations.

Furthermore, testing of single receptor subunits with a variety of potential agonists or antagonists would provide additional information with respect to the function and activity of the individual subunits. Such information may lead to the identification of compounds which are capable of very specific interaction with one or more of the receptor subunits. Such specificity may prove of great value in medical application.

In accordance with one aspect of the present invention, assay methods have been developed for the ready determination of the presence of functional neuronal nicotinic acetylcholine receptors. Thus, cells transformed with invention DNA or RNA sequences, or cell-lines derived from a variety of other sources can be readily screened to determine if functional receptors are produced thereby. One useful assay method is the "$^{86}$Rb ion-flux" assay, wherein the influx of $^{86}$Rb ions into test cells is measured as a function of the presence or absence of known neuronal nicotinic acetylcholine agonists or antagonists. Thus, a cell which shows no difference in the $^{86}$Rb ion flux, whether in the presence or absence of agonist or antagonist is not expressing functional neuronal receptor. This assay provides more inforamtion than is provided by a simple binding assay because it also indicates whether or not functional receptor is present.

Another useful assay method of the invention involves subjecting test cells to the following steps:

(a) analyzing said cells for the presence of alpha and beta subunits RNAs, (b) analyzing those cells which are positive for the presence of alpha and beta subunit RNAs for their ability to bind nicotine or a nicotine agonist, relative to the nicotine binding ability of control cells known to produce neuronal nicotinic acetylcholine receptors, and (c) determining the effect of known neuronal nicotinic acetylcholine agonists and/or antagonists on cells having the ability to bind nicotine or nicotine agonist on the influx of $^{86}$Rb ions into said cells, relative to the rate of influx of $^{86}$Rb ions into positive and/or negative control cells.

Cells can be analyzed for the presence of alpha and beta subunit RNA in a variety of ways, such as for example, by Northern hybridization, slot blot analysis, and the like.

The determination of the nicotine-binding ability of test cells can readily be determined by techniques known by those of skill in the art. For additional detail, see Example 3B below.

The $^{86}$Rb ion-flux assay is then carried out as described hereinabove.

The above-described sequence of analytical steps provides an effective way to screen large numbers of transformed cells for the expression of neuronal receptor subunit (s), the ability of such subunit(s) to bind to nicotine, nicotine agonists or nicotine antagonists, and the ability of such subunit(s) to assemble into functional receptors.

As a further step to verify the ability of test cells to produce functional receptor, mRNA from cells which are positive for the presence of alpha and beta neuronal nicotinic acetylcholine receptor subunits by the above-described assays can be injected into oocytes, which can then be assayed for the presence of functional neuronal nicotinic acetylcholine receptors. As another alternative, one can measure the electrophysiology of the positive cells (either directly or upon expression of RNA by oocytes). Positive results in each of these assays provides one with a high level of confidence that the test cells contain the coding sequences for the production of receptor, and that such receptor is indeed expressed.

In accordance with another aspect of the present invention, a method for making eukaryotic cells having neuronal nicotinic acetylcholine receptor activity is provided. Eukaryotic cells (e.g., mammalian or yeast cells) are transfected with DNA encoding at least one alpha subunit and at least one beta subunit of the neuronal nicotinic acetylcholine receptor. The resulting cells are then screened by one or more of the above-described assay methods to identify those cells which have successfully incorporated the desired DNA sequences.

The invention will now be described in greater detail by reference to the following non-limiting examples.

EXAMPLES

Plasmids comprising insert DNA encoding human α and β subunit proteins of the neuronal nicotinic acetylcholine receptor (nNAChR), isolated from various sources of human neuronal tissue, have been deposited in the ATCC. The clone names and deposit numbers are:

| Subunit | Clone Name | ATCC Accession # |
|---------|------------|------------------|
| α2 | HnAChRα2 | 68277 |
| α3 | HnAChRα3 | 68278 |
| β2 | HnAChRβ2 | 68279 |

Restriction maps of the nNAChR-encoding inserts in these clones, as compared to the corresponding rat cDNA maps, are provided in FIGS. 1, 2, and 3, respectively. The rat cDNA inserts are described in Wada et al. (1988), *Science* 240:330–334 (α2); Boulter et al. (1986), *Nature* 319:368–374 (α3); Boulter et al. (1987), *Proc. Natl. Acad. Sci.* 84:7763–7767 (β2). EcoRI adapters (from cloning vector) are present on the ends of each insert.

Portions of the α2 and α3, and all of the β2, human neuronal NAChR subunit-encoding sequence were sequenced. The sequences of the human cDNAs were compared to the corresponding regions of the rat cDNAs, and the percent homology between the human and rat sequences are provided in FIGS. 4, 5, and 6, respectively. The nucleotide sequence homology is presented outside the parentheses, the translated amino acid sequence homology is presented in parentheses.

Additionally, actual nucleotide sequence comparisons are presented in FIGS. 7, 8 and 9. In all figures the human sequence is on top and the rat sequence is on the bottom. The nucleotide numbers for the rat sequences correspond to the actual nucleotide positions in the coding sequence. In contrast, the nucleotide numbers for the human sequences do not correspond to the coding sequences; instead, these numbers are related to the individual sequenced fragments.

FIG. 7 presents the nucleotide sequence of the human α2 sequence as compared to the rat α2 sequence starting around the common BamHI site (see FIG. 4) and continuing in the 3' direction approximately 500 nucleotides. The degree of nucleotide homology in section A of FIG. 7 is 87% and in section B is 93%.

FIG. 8 presents the nucleotide sequence of the human α3 sequence starting about 50 nucleotide 3' from the 5' end of the coding sequence, and continuing in the 3' direction for about 650 nucleotides. The degree of nucleotide homology between the human and rat sequence in Section A is 86% and in Section B is 90%.

FIG. 9 presents the entire coding sequence of the cDNA encoding the human β2 subunit. It has 87% homology to the rat sequence at the nucleotide level.

Example 1

Construction of Eukaryotic Expression Vectors Comprised of the Human Neuronal NAChR Subunit Sequences The cDNAs encoding the human neuronal NAChR subunits were inserted into the eukaryotic expression vector pSV2+Ldhfr, the construction of which is described in Example 2. Each insert was excised from its plasmid (HnAchRα2, HnAchRα3, or HnAchβ2) by digestion with EcoRI. The resultant fragments were gel purified and the ~2600 bp (α2), ~3200 bp (α3), and ~2450 bp (β2) fragments were isolated. Each insert fragment was ligated to EcoRI-digested and dephosphorylated pSV2+Ldhfr; 0.1 μg of each DNA was used. The ligation reaction was transformed into MC1061 cells and amp$^R$ colonies were selected. The desired plasmid(s) having insert in the correct orientation was (were) identified by the diagnostic fragments provided below, and named as follows:

| Subunit | Plasmid name | Diagnostic fragment |
|---------|--------------|---------------------|
| α2 | hα2/pSV2 | PvuII: 550, 100, 7000 bp |
| α3 | hα3/pSV2 | PvuII: 850, 7350 bp |
| β2 | hβ2/pSV2 | HindIII: 450, 7000 bp |

These plasmids have the subunit-encoding insert placed in functional association downstream of the SV40 early promoter.

Example 2

Development of Mammalian Cell Lines Expressing α and β Subtypes of the Rat Neuronal Nicotinic Acetylcholine Receptor (rNAChR)

Cell lines were developed in Ltk$^-$ (mouse fibroblast thymidine kinase deficient) cells by cotransfecting a plasmid comprised of an α-subunit-encoding sequence, a plasmid comprised of a β-subunit-encoding sequence, and a plasmid comprised of either the wild-type or crippled TK gene. A reporter gene expression construct can also be cotransfected into the cells to provide a transcription-based assay system. While the following examples employ eukaryotic expression vectors comprised of the rat NAChR subunit cDNA sequences, the eukaryotic expression vectors comprised of the human nNAChR cDNA sequences (Example 1) also can be used.

A. Host Cells

Ltk$^-$ cells are available from ATCC (accession #CCL1.3).

B. rNAChR α- and β-Expression Plasmids

The α- and β-encoding eukaryotic expression plasmids were constructed using a slightly modified pSV2dhfr parent plasmid [Subramani, et al. (1981). *Mol. Cell. Biol.* 1:854–864] and α- and β-encoding inserts from the rat nNAChR subunit clones. The clone sources for the subunit sequences were:

| Subunit | Parent plasmid | Insert fragment |
|---|---|---|
| α2 | HYP16(9)$^a$ | ~2 Kb EcoRI |
| α3 | PCA48E(4)$^b$ | ~2 Kb HindIII-EcoRI |
| *α4.1 | HYA23-1E(1)$^c$ | ~2 Kb HindIII |
| β2 | PCx49(1)$^d$ | ~2 Kb EcoRI |

$^a$Wada et al., supra
$^b$Boulter et al., (1986), supra
$^c$Goldman et al., (1987), Cell 48:965–973
$^d$Boulter et al., (1987), supra
*This insert was placed into unmodified pSV2dhfr.

The pSV2dhfr plasmid was modified by first destroying the unique EcoRI site, then inserting a HindIII-EcoRV-EcoRI polylinker between the SV40 early promoter and the dhfr gene. To accomplish this, pSV2dhfr was cut with EcoRI, Klenow-treated, and religated. The resultant plasmid was called pSV2dhfrΔRI. Plasmid pSV2dhfrΔRI was digested with HindIII and 0.1 μg was ligated with a 100:1 molar ratio of unkinased double-stranded oligonucleotide of the following sequence:

```
AGC TTT CGA TAT CAG AAT TCG        (SEQ ID NO:11)
    AA GCT ATA GTC TTA AGCTCGA    (SEQ ID NO:12)
    HindIII EcoRV    EcoRI   destroyed HindIII
```

The ligation reaction was transformed into MC1061 bacterial cells, amp$^R$ colonies were selected, and plasmid was isolated. Correctly modified plasmid demonstrated a 350 bp band upon digestion with PvuII/EcoRI, and was called pSV2+Ldhfr.

To create the α2, α3, and β2 expression plasmids, 0.1 μg of pSV2+Ldhfr, or pSV2dhfr in the case of α4, and 0.1 μg of the subunit specific gel-isolated insert fragment were ligated, and the individual ligations were separately transformed into MC1061 cells. (The parent plasmids were digested with the appropriate enzyme to allow insertion of the insert noted above into the polylinker site prior to ligation). Amp$^R$ colonies were selected and plasmid was isolated. The final plasmid names and diagnostic bands indicative of the correct orientation were:

| Subunit | Plasmid name | Diagnostic fragments |
|---|---|---|
| α2 | pSV2dhfrα2 | 1600 bp BglII |
| α3 | pSV2dhfrα3 | 600 bp PvuII;850 bp BamHI |
| α4 | pSV2dhfrα4 | 800 bp PvuII/SstI |
| β2 | pSV2dhfrβ2 | 1800 bp PvuII |

These final plasmids have the subunit insert placed in functional association downstream of the SV40 early promoter.

C. TK$^+$ Selection Plasmids

The TK$^+$ plasmid cotransfected into Ltk$^-$ cells along with the nNAChR subunit-expressing plasmids was either pThx59 [Zipser, et al., *Proc. Natl. Acad. Sci.* 78:6276–6280 (1981)] which encodes the wildtype TK gene, or pThx24 (ibid.) which encodes a crippled TK gene.

D. Reporter Gene Expression Plasmid

A reporter gene expression plasmid comprised of the CAT gene regulated by the c-fos promoter, plasmid pFC4 [(Deschamps et al., *Science* 230:1174–1177 (1985)], can also be cotransfected into the cells.

E. Transfection and TK$^+$ Selection

The CaPO$_4$ transfection procedure used in the development of the rat nNAChR-expressing cell lines was that of Wigler, et al. (1979), *Proc. Natl. Acad. Sci.* 76:1373–1376.

Briefly, Ltk$^-$ cells were grown in nonselective medium [D+10 (Dulbecco's modified Eagle's medium+10% calf serum), 100 U/ml penicillin, and 100 μg/ml streptomycin] in a 10 cm-sized dish, to 20% confluence. The three circular vector DNAs were precipitated with CaPO$_4$ and added to the cell monolayer. The vector concentrations were as follows:

Thx24:α$_x$β$_2$ 2μg:2μg:2μg/ml

Thx59:α$_x$β$_2$ 0.25μg:2μg:2μg/ml

The transfected cells were allowed to grow for two days in nonselective medium. After two days, the cells were passed and non-selective media was replaced with selective HAT medium (D+10+15 μg/ml hypoxanthine+1 μg/ml aminopterin+5 μg/ml thymidine), and the cells were left to grow for 10–15 days, during which time the cells were "fed" fresh selective (HAT) medium every 3–4 days. After 10–15 days, colonies appeared which indicated acceptance and expression of at least the plasmid carrying the TK gene. Colonies were transferred into separate wells of a 24-well dish and grown in selective medium for seven days, at which time individual colonies were passed into 6-well dishes and grown for another seven days in selective medium. To provide cells for freezing and subsequent molecular and functional receptor analyses, the individual clones in the 6-well dishes were passed to 100 ml dishes in selective medium for 5–7 days.

Example 3

Characterization of Cell Lines Expressing NAChR

The cell lines developed according to the methods of Example 2 were characterized using one or more of the methods described below.

A. Northern or Slot Blot Analysis for Expression of α- and β- Subunit Encoding Messages Total RNA was isolated from 1×10$^7$ cells and 10–15 μg of RNA from each cell type were used for Northern or slot blot hybridization analysis. The inserts from the rat nNAChR-encoding plasmids were nick-translated and used as probe. In addition, the β-actin gene sequence [(Cleveland et al., *Cell* 20:95–105 (1980)] was nick-translated and used as a control probe on duplicate filters to confirm the presence or absence of RNA on each blot and to provide a rough standard for use in quantitating differences in α- or β-specific mRNA levels between cell lines. The Northern and slot blot hybridization and wash conditions were as follows:

Hybridization: 5XSSPE, 5X Denhardts,
50% formamide, 42° C.
Wash: 0.2XSSPE, 0.1% SDS, 65° C.

The results of these analyses showed that, while the amount of counts per minute corresponding to actin message was fairly constant among the various cells lines, the levels of α- and β-specific messages varied. Cell lines testing positive for both α- and β-specific mRNA were further tested for functional receptors.

B. Nicotine-Binding Assay

Cell lines which demonstrated α- and β-specific mRNA were analyzed for their ability to bind nicotine, as compared to three control cell lines: the neuronally-derived cell lines PC12 (Boulter et al., (1986), supra) and IMR32 (Clementi, et al. (1986); *Int. J. Neurochem* 47:291–297, and the muscle-derived cell line BC3H1 (Patrick, et al., (1977); *J. Biol. Chem.* 252:2143–2153). The assay was conducted as follows:

Just prior to being assayed, the transfected cells were removed from plates by scraping. PC12, BC3H1, and IMR32 (which had been starved for fresh media for seven days). Control cell lines were removed by rinsing in 37° C. assay buffer (50 mM Tris/HCl, 1 mM $MgCl_2$, 2 mM $CaCl_2$, 120 mM NaCl, 3 mM EDTA, 2 mg/ml BSA and 0.1% aprotinin at pH7.4). The cells were washed and resuspended to a concentration of $1 \times 10^6/250$ μl. To each plastic assay tube was added 250 μl of the cell solution, 15 nM $^3$H-nicotine, with or without 1 mM cold nicotine, and assay buffer to make a final volume of 500 μl. The assays for the transfected cell lines were incubated for 30 min at room temperature; the assays of the positive control cells were incubated for 2 min at 1° C. After the appropriate incubation time, 450 μl aliquots of assay volume were filtered through Whatman GF/C glass fiber filters which had been pretreated by incubation in 0.05% polyethyleneimine for 24 hours at 4° C. The filters were then washed twice, with 4 ml each wash, with ice cold assay buffer. After washing, the filters were dried, added to vials containing 5 ml scintillation fluid and then counted.

The $IC_{50}$ values for displacement of specifically bound $^3$H-nicotine in the three control cell lines were:

| Cell line | Nicotine concentration required to displace 50% bound nicotine ($IC_{50}$) |
|---|---|
| BC3H1 | 90 μM |
| PC12 | 40 μM |
| IMR32 | 35 μM |

C. $^{86}$Rb Ion-Flux Assay

The ability of nicotine or nicotine agonists and antagonists to mediate the influx of $^{86}$Rb into transfected and control cells has been found to provide an indication of the presence of functional NAChRs on the cell surface. The $^{86}$Rb ion-flux assay was conducted as follows:

1. The night before the experiment, the cells were plated at $2 \times 10^6$ per well (i.e., 2 ml per well) in a 6-well polylysine-coated plate.

2. The culture medium was decanted and the plate was washed with 2 ml of assay buffer (50 mM hepes, 260 mM sucrose, 5.4 mM KCl, 1.8 mM $CaCl_2$, 0.8 mM $MgSO_4$, 5.5. mM glucose) at room temperature.

3. The assay buffer was decanted and 1 ml of assay buffer, containing 2 μCi/ml $^{86}$Rb, with 5 mM ouabain and agonist or antagonist in a concentration to effect a maximum response, was added.

4. The plate was incubated on ice at 1° C. for 4 min.

5. The buffer was decanted into a waste container and each well was washed with 3 ml of assay buffer, followed by two washes of 2 ml each.

6. The cells were lysed with $2 \times 0.5$ ml of 0.2% SDS per well and transferred to a scintillation vial containing 5 ml of scintillation fluid.

7. The vials are counted and the data calculated.

The positive control cells provided the following data in this assay:

| | PC12 | | IMR32 | |
|---|---|---|---|---|
| | $EC_{50}$ | Maximum response | $EC_{50}$ | Maximum response |
| Agonist | | | | |
| nicotine | 52 μM | 2.1X[a] | 18 μM | 7.7X[a] |
| carbamylcholine (CCh) | 35 μM | 3.3X[b] | 230 μM | 7.6X[c] |
| cytisine | 57 μM | 3.6X[d] | 14 μM | 10X[e] |
| Antagonist | | | | |
| d-tubocurarine | 0.81 μM | | 2.5 μM | |
| mecamylamine | 0.42 μM | | 0.11 μM | |
| hexamethonium | nd[f] | | 22 μM | |
| atropine | 12.5 μM | | 43 μM | |

[a] 200 μM nicotine
[b] 300 μM CCh
[c] 3 mM CCh
[d] 1 mM cytisine
[e] 100 μM cytisine
[f] nd = not determined

D. Nicotine-Induced c-fos Promoted Expression of CAT

In cell lines developed by cotransfection of the pFC4 c-fos-CAT plasmid along with the nNAChR subunit-encoding plasmids and the marker plasmid, the functionality of the nNAChRs can be indirectly evaluated by measuring the level of CAT activity. The CAT activity assay can be performed by any of the known methods in the art. See, for example, Nielsen et al., *Anal. Biochem.* 179:19–23 (1989).

E. Xenopus oocytes Assay

The functionality of the nNAChR expressed in transfected cells or encoded by the human neuronal NAChR subunit-encoding cDNAs can be evaluated in the Xenopus oocytes system. See Dascal, N. (1987), *CRC Crit. Rev. Biochem.* 22:317–387, for a review of the use of Xenopus oocytes to study ion channels. RNA from transfectant cell lines or transcribed in vitro from the subunit-encoding cDNAs is injected into oocytes for translation into functional protein. The function of the expressed nNAChR can be assessed by a variety of electrophysiological techniques, including intracellular voltage recording, two-electrode voltage clamp, and patch clamp methods. The cation-conducting channel intrinsic to the NAChR opens in response to acetylcholine (ACh) or other nicotinic cholinergic agonists, permitting the flow of transmembrane current carried predominantly by sodium and potassium ions under physiological conditions. This current can be monitored directly by the voltage clamp techniques, or indirectly by intracellular voltage recording, wherein changes in membrane potential due to the net entry of cations are measured. With the intracellular voltage method, perhaps the simplest technique, a depolarization is recorded upon external application of agonist, signifying the presence of functional receptors in the oocyte membrane.

In a typical experiment to evaluate the functionality of nNAChR subunit-encoding transcripts, 15 oocytes were injected with ~5 ng of a 1:1 mixture of an a and a β transcript. Other oocytes were injected with water to serve as negative controls. The oocytes were then incubated at 19° C. for 2–5 days in OR-2, an oocyte Ringer's solution of the following composition (concentration in mM): NaCl, 82.5; KCl, 2.5; $Na_2HPO_4$, 1; HEPES, 5; $CaCl_2$, 1; $MgCl_2$, 1; pH=7.8. For electrophysiological recording, OR-2 of identical composition except at pH=7.5 was used as the basis of drug-containing solutions of the bath and agonist application pipet. During continuous intracellular voltage recording in a bath of OR-2 containing 1 μM atropine to block endogenous muscarinic acetylcholine receptor responses, a pipet containing 100 μM ACh was used to intermittently apply ACh by a local perfusion method in which the ACh is diluted by a factor of about 3–10 upon application to the oocyte.

Healthy oocytes have resting potentials in the range of −50 to −70 mV. Depolarizations due to ACh ranged from several mV to about 30 mV in different batches of oocytes injected with NAChR subunit-encoding transcripts. (Responses within a given batch of oocytes tended to be of similar magnitude). The depolarizing responses to ACh were reversibly blocked by 100 $\mu$M d-tubocurarine, added to the bath. By contrast, water-injected oocytes did not respond at all to ACh administration under these conditions.

In a typical experiment to evaluate the nNAChR subunit-encoding RNA from transfected cell lines, total RNA was isolated from the cells and 50 ng were injected into oocytes. The oocytes were incubated and treated with acetylcholine, atropine, and d-tubocurarine as described above. Negative control oocytes were injected with RNA from a negative control cell line transfected with parent plasmid lacking a nNAChR subunit-encoding insert.

Oocytes injected with message from nNAChR-transfected cells demonstrated depolarization when treated with acetylcholine. The depolarization was blocked with d-tubocurarine. The negative control oocytes were unresponsive, as expected.

Alternatively, the functionality of nNAChRs expressed in transfected cells can be studied by standard electrophysiological techniques such as intracellular voltage recording or patch clamp, analogous to the methods described for oocytes.

Example 4

Cell Lines Expressing Functional nNAChRs

Several cell lines were generated employing the procedures of Example 2. The resulting cell lines were then analyzed employing the assay methods described in Example 3. Results for several newly prepared cell clones are summarized below:

| Cell line | Subunits | RNA analysis | Binding | Rb flux | Oocytes |
|---|---|---|---|---|---|
| 592F | $\alpha 2\beta 2$[a] | +/+[b] | +[c] | nd | +[d] |
| 243C | $\alpha 3\beta 2$ | +/+ | + | nd | + |
| 244A | $\alpha 4\beta 2$ | +/+ | + | nd | + |
| 244I | $\alpha 4\beta 2$ | +/+ | + | nd | nd | nd = not determined
[a] subunits are from rat NAChR
[b] +/+ indicates that $\alpha$- and $\beta$-specific mRNA was detected
[c] + indicates that the cell line binds agonist in a manner similar to positive control cells
[d] + indicates that ACh induces membrane depolarization which was blocked by d-tubocurarine.

These results show that functional nNAChRs are expressed by mammalian cells transfected with DNA encoding an $\alpha$-subunit and a $\beta$-subunit of the nNAChR.

The invention has been described in detail with reference to certain particular embodiments thereof. It will be understood, however, that variations and modifications can be effected within the spirit and scope of the invention.

We claim:

1. An isolated nucleic acid molecule, comprising a sequence of nucleotides encoding a beta2 subunit of a human neuronal nicotinic acetylcholine receptor.

2. An isolated and purified human neuronal nicotinic acetylcholine receptor subunit encoded by the alpha3-encoding nucleic acid in a plasmid having all of the identifying characteristics of HnAChRα3 deposited under ATCC Accession No. 68278.

3. An isolated and purified human neuronal nicotinic acetylcholine receptor subunit encoded by the beta2-encoding nucleic acid in a plasmid having all of the identifying characteristics of HnAChRα3 deposited under ATCC Accession No. 68279.

4. A method of making cells having neuronal nicotinic acetylcholine receptor activity, comprising:
   (a) introducing one or more nucleic acid molecules that encode(s) at least one alpha subunit of a neuronal nicotinic acetylcholine receptor and at least one beta subunit of a neuronal nicotinic acetylcholine receptor into eukaryotic cells, wherein the nucleic acid encoding an alpha subunit comprises a sequence of amino acids encoded by the alpha3-encoding nucleic acid that is isolated from a plasmid having all of the identifying characteristics of HnAChRα3 deposited under ATCC Accession No. 68278, and the nucleic acid encoding the beta subunit comprises a sequence of amino acids encoded by SEQ ID No. 9;
   (b) selecting cells from (a) that express the alpha or the beta encoding nucleic acid or express the alpha and beta subunit-encoding nucleic acid; and
   (c) detecting neuronal nicotinic acetylcholine receptor activity in the selected cells, wherein the activity is mediated by a receptor containing one or more of the alpha and beta subunits encoded by said introduced nucleic acid molecules.

5. An isolated nucleic acid molecule, comprising the alpha2-encoding nucleic acid open reading frame that is isolated from a plasmid having all of the identifying characteristics of HnAChRα2 deposited under ATCC Accession No. 68277.

6. An isolated nucleic acid molecule, comprising a sequence of nucleotides encoding an alpha3 subunit of a human nicotinic acetylcholine receptor that is encoded by the alpha3-encoding nucleic acid that is isolated from a plasmid having all of the identifying characteristics of HnAChRα3 deposited under ATCC Accession No. 68278.

7. An isolated cell, comprising the nucleic acid molecule of claim 6.

8. The cell of claim 7 that is a bacterial cell, mammalian cell, yeast cell or amphibian oöcyte.

9. The cell of claim 7 further comprising a nucleic acid molecule that encodes a beta subunit of a human nicotinic acetylcholine receptor, wherein the beta subunit comprises a sequence of amino acids encoded by SEQ ID No. 9.

10. A method for screening compounds for activity as nicotinic acetylcholine receptor agonists or antagonists, said method comprising:

contacting a cell of claim 7 with a test compound, and thereafter monitoring nicotinic acetylcholine receptor activity of the cell by monitoring the performance of the cell by measuring a performance parameter selected from the group consisting of the flux of ions through the membrane of the cell, nicotine binding to nicotinic acetylcholine receptors of the cell, or the electrophysiological response of the cells, wherein the cell expresses a nicotinic acetylcholine receptor that contains a subunit encoded by the nucleic acid molecule.

11. The method of claim 10, wherein the cell further comprises DNA encoding a beta2 subunit of a human nicotinic acetylcholine receptor comprising a sequence of amino acids encoded by SEQ ID No.9.

12. The method of claim 10, wherein, prior to contacting the cells with a test compound, the cells are contacted with a nicotinic acetylcholine receptor agonist.

13. The cell of claim 7, further comprising a reporter gene expression construct; and the reporter gene expression construct comprises:

a transcriptional control element, and a reporter gene encoding a transcriptional and/or translational product;

the transcriptional control element, in said cell, is responsive to an intracellular condition that occurs when a human neuronal nicotinic acetylcholine receptor interacts with a compound having agonist or antagonist activity with respect to said receptor;

said product can be, directly or indirectly, detected; and the reporter gene is in operative association with said transcriptional control element.

14. A method for screening test compounds for activity as nicotinic acetylcholine receptor agonists or antagonists, comprising:

comparing the difference in the amount of transcription of a reporter gene in the cells of claim 13 in the presence of the compound with the amount of transcription in the absence of the compound or with the amount of transcription in the control cells that do not express nicotinic acetylcholine receptors, but contain the reporter gene expression construct, wherein compounds that exhibit activity as agonists or antagonists are identified.

15. The method of claim 14, wherein, prior to comparing the difference in the amount of transcription, the cells are contacted with a nicotinic acetylcholine receptor agonist.

16. The method of claim 15, wherein the agonist is nicotine.

17. The cell of claim 7 that is a eukaryotic cell.

18. The cell of claim 17 that is a mammalian cell, yeast cell or amphibian oocyte.

19. The cell of claim 7 that is a bacterial cell.

20. An isolated nucleic acid molecule, comprising a sequence of nucleotides encoding a beta2 subunit of a human nicotinic acetylcholine receptor that is encoded by the beta2-encoding nucleic acid that is isolated from a plasmid having all of the identifying characteristics of HnAChRβ2 deposited under ATCC Accession No. 68279 or the sequence of nucleotides set forth as nucleotides 1–1521 in SEQ ID No. 9.

21. An isolated cell, comprising the nucleic acid molecule of claim 20.

22. The cell of claim 21 that is a eukaryotic cell.

23. An isolated cell, comprising the nucleic acid of claim 21.

24. The cell of claim 23 that is a eukaryotic cell.

25. The cell of claim 24 that is a mammalian cell, yeast cell or amphibian oocyte.

26. The cell of claim 25 that expresses a nicotinic acetylcholine receptor comprising a subunit encoded by the nucleic acid.

27. The cell of claim 23 that is a bacterial cell.

28. An isolated and purified protein encoded by the alpha2-encoding nucleic acid open reading frame that is isolated from a plasmid having all of the identifying characteristics of HnAChRα2 deposited under ATCC Accession Number 68277.

29. An isolated and purified subunit of a human nicotinic acetylcholine receptor encoded by the alpha3-encoding nucleic acid open reading frame that is isolated from a plasmid having all of the identifying characteristics of HnAChRα3 deposited under ATCC Accession Number 68278.

30. An isolated and purified subunit of a human nicotinic acetylcholine receptor encoded by the beta2-encoding nucleic acid open reading frame that is isolated from a plasmid having all of the identifying characteristics of HnAChRβ2 deposited under ATCC Accession Number 68279 or the sequence of nucleotides set forth as nucleotides 1–1521 of SEQ ID NO:9.

31. A plasmid having all of the identifying characteristics of the plasmid deposited under ATCC Accession No. 68277.

32. An isolated nucleic acid molecule, comprising the sequence of nucleotides set forth in SEQ ID No. 9.

33. An isolated nucleic acid molecule, comprising a sequence of nucleotides that encodes a beta2 subunit of a human nicotinic acetylcholine receptor, wherein the beta2 subunit comprises the sequence of amino acids encoded by the sequence of nucleotides set forth as nucleotides 1–1521 in SEQ ID No. 9.

34. An isolated and purified beta2 subunit of a human nicotinic acetylcholine receptor encoded by a nucleic acid molecule, comprising a sequence of nucleotides that encodes a beta2 subunit of a human nicotinic acetylcholine receptor, wherein the beta2 subunit comprises a sequence of amino acids encoded by the sequence of nucleotides set forth in SEQ ID No. 9.

35. An isolated nucleic acid, comprising the sequence of nucleotides set forth in SEQ ID No. 1.

36. An isolated nucleic acid, comprising the sequence of nucleotides set forth in SEQ ID No. 3.

37. An isolated nucleic acid, comprising the sequence of nucleotides set forth in SEQ ID No. 5.

38. An isolated nucleic acid, comprising the sequence of nucleotides set forth in SEQ ID No. 7.

39. An isolated nucleic acid molecule encoding a beta2 subunit of a human neuronal nicotinic acetylcholine receptor, comprising the sequence of nucleotides set forth in SEQ ID No. 9.

40. A plasmid having all of the identifying characteristics of the plasmid deposited under ATCC Accession No. 68278.

41. A plasmid having all of the identifying characteristics of the plasmid deposited under ATCC Accession No. 68279.

* * * * *

UNITED STATES PATENT AND TRADEMARK OFFICE
CERTIFICATE OF CORRECTION

| | | |
|---|---|---|
| PATENT NO. | : 5,981,193 | Page 1 of 2 |
| APPLICATION NO. | : 07/938154 | |
| DATED | : November 9, 1999 | |
| INVENTOR(S) | : Harpold et al. | |

It is certified that error appears in the above-identified patent and that said Letters Patent is hereby corrected as shown below:

Title page
IN THE REFERENCES CITED, ITEM [56]

Please add the following in the Other Publications:

-- EMBASE abstract #90191445, Kouzarides *et al.* Behind the Fos an Jun Leucine zipper, *Cancer Cells USA* 1(3):71-76 (1989).

Gorman *et al.,* Recombinant genomes which express chloramphenicol acetyltransferase in mammalian cells, *Mol. Cell. Biol.* 2(9): 1044-1051 (1982). --

Figure 4A:
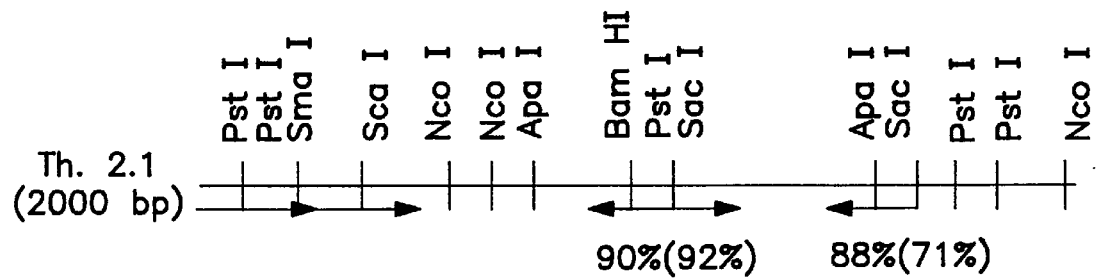
FIG. 4 is a comparison of the alpha2 subunit gene of the rat neuronal nicotinic acetylcholine receptor with several cDNA fragments obtained from the human alpha2 subunit gene. The arrows beneath the various human cDNA fragments indicate the direction and extent of DNA sequencing carried out for the respective fragments.
Figure 4B:
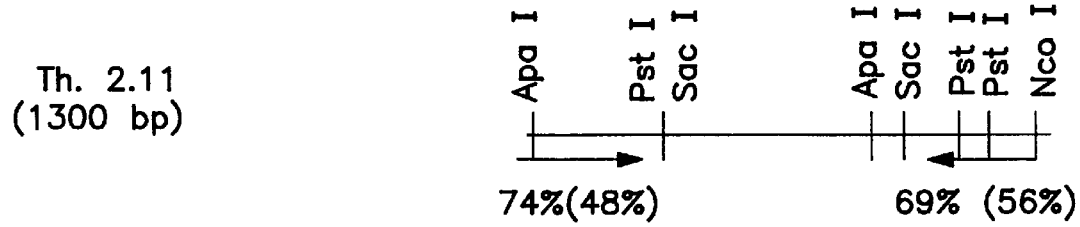
Figure 4C:
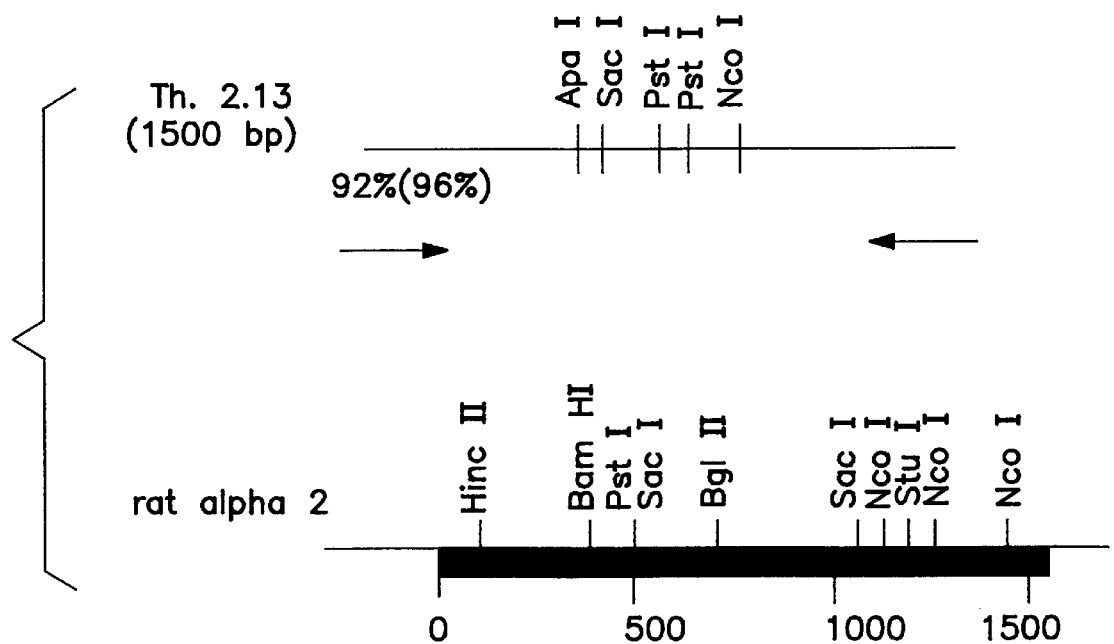
Figure 5A:
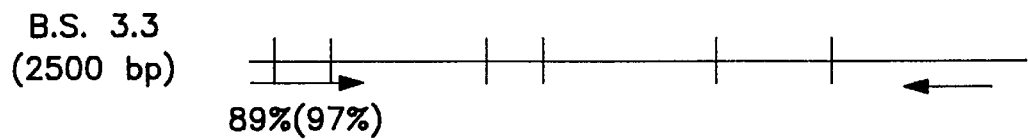
FIG. 5 is a comparison of the alpha3 subunit gene of the rat neuronal nicotinic acetylcholine receptor with several cDNA fragments obtained from the human alpha3 subunit gene. The arrows beneath the various human cDNA fragments indicate the direction and extent of DNA sequencing carried out for the respective fragments.
Figure 5B:
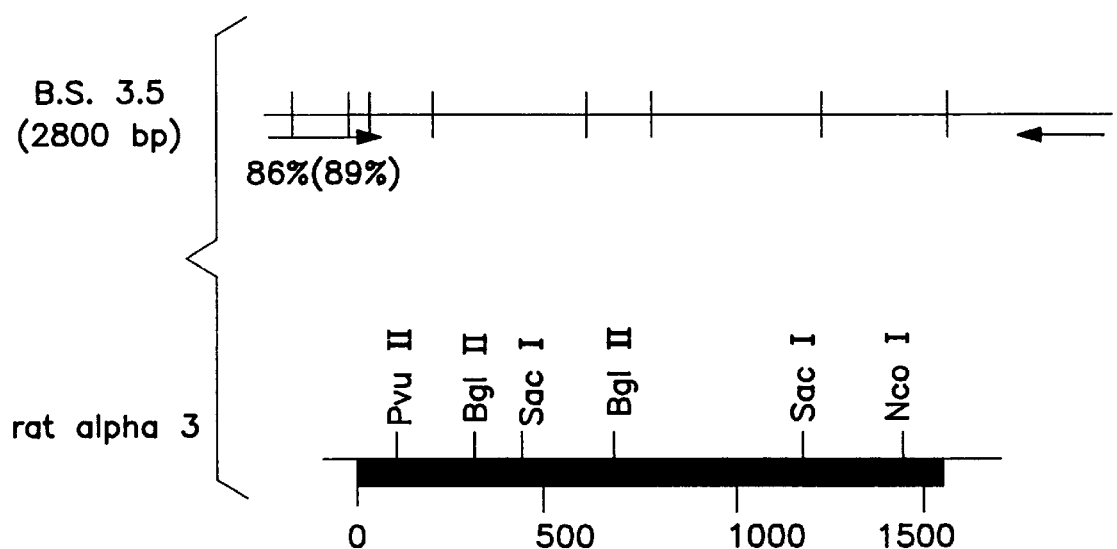
Figure 6A:
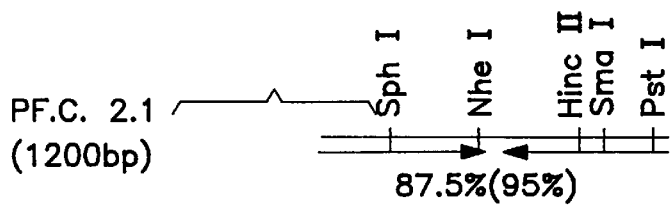
FIG. 6 is a comparison of the beta2 subunit gene of the rat neuronal nicotinic acetylcholine receptor with several cDNA fragments obtained from the human beta2 subunit gene. The arrows beneath the various human cDNA fragments indicate the direction and extent of DNA sequencing carried out for the respective fragments.
Figure 6B:
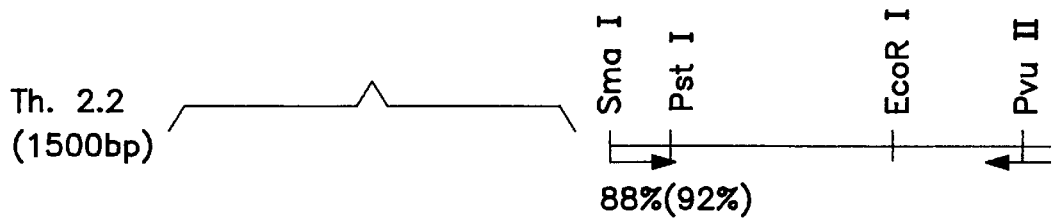
Figure 6C:
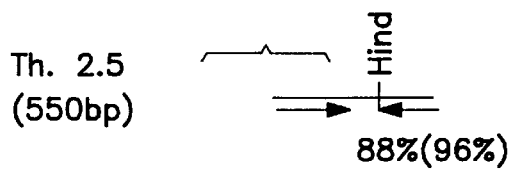
Figure 6D:
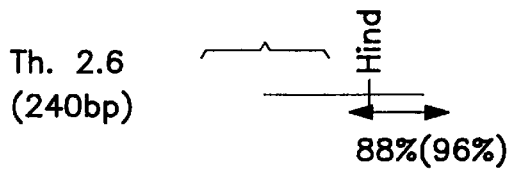
Figure 6E:
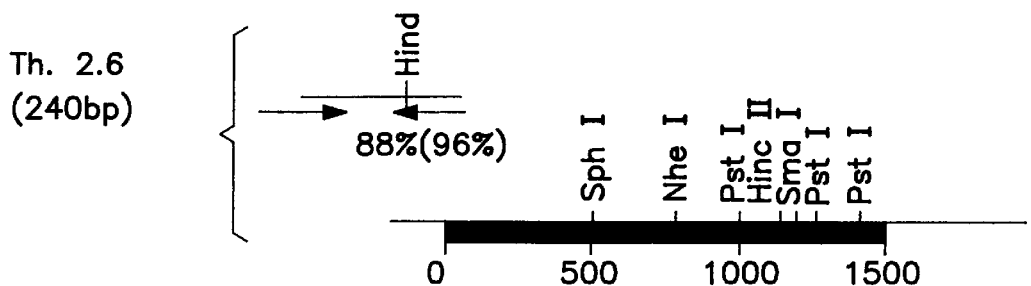

IN THE SPECIFICATION:

at column 3, line 66, please replace "Figure 4" with -- Figure 4A-C --;

at column 4, line 5, please replace "Figure 5" with -- Figure 5A-B --;

at column 4, line 11, please replace "Figure 6" with -- Figure 6A-E --;

at column 4, line 17, please replace "Figure 7" with -- Figure 7A-B --;

at column 4, line 19, please replace "Figure 8" with -- Figure 8A-B --;

at column 4, line 21, please replace "Figure 9" with -- Figure 9A-E --;

at column 5, line 61, please replace "Figure 7" with -- Figure 7A-B --;

at column 6, line 1, please replace "Figure 8" with -- Figure 8A-B --;

at column 6, line 8, please replace "Figure 9" with -- Figure 9A-E --;

at column 6, line 59, please replace "hight" with -- high --;

at column 7, line 2, please replace "Figures 4, 5 and 6" with -- Figures 4A-C, 5A-B and 6A-E --;

UNITED STATES PATENT AND TRADEMARK OFFICE
CERTIFICATE OF CORRECTION

| | |
|---|---|
| PATENT NO. | : 5,981,193 |
| APPLICATION NO. | : 07/938154 |
| DATED | : November 9, 1999 |
| INVENTOR(S) | : Harpold et al. |

It is certified that error appears in the above-identified patent and that said Letters Patent is hereby corrected as shown below:

at column 9, line 57, please replace "Figures 4, 5 and 6" with -- Figures 4A-C, 5A-B and 6A-E --;

at column 9, line 62, please replace "Figures 7, 8 and 9" with -- Figures 7A-B, 8A-B and 9A-E --;

at column 10, line 6, please replace "Figure 7" with -- Figure 7A-B --;

at column 10, line 8, please replace "Figure 8" with -- Figure 8A-B --;

at column 10, line 9, please replace "Figure 9" with -- Figure 9A-E --;

IN THE CLAIMS:

Please replace claim 3 with the following claim:

-- 3. An isolated and purified human neuronal nicotinic acetylcholine receptor subunit encoded by the beta 2-encoding nucleic acid in a plasmid having all of the identifying characteristics of HnAChRβ2 deposited under ATCC Accession No. 68279. --

Signed and Sealed this

Twenty-eighth Day of October, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,981,193 | Page 1 of 2 |
| APPLICATION NO. | : 07/938154 | |
| DATED | : November 9, 1999 | |
| INVENTOR(S) | : Harpold et al. | |

It is certified that error appears in the above-identified patent and that said Letters Patent is hereby corrected as shown below:

Title page
IN THE REFERENCES CITED, ITEM [56]

Please add the following in the Other Publications:

-- EMBASE abstract #90191445, Kouzarides *et al.* Behind the Fos an Jun Leucine zipper, *Cancer Cells USA* 1(3):71-76 (1989).

Gorman *et al.*, Recombinant genomes which express chloramphenicol acetyltransferase in mammalian cells, *Mol. Cell. Biol.* 2(9): 1044-1051 (1982). --

IN THE SPECIFICATION:

at column 3, line 66, please replace "Figure 4" with -- Figure 4A-C --;

at column 4, line 5, please replace "Figure 5" with -- Figure 5A-B --;

at column 4, line 11, please replace "Figure 6" with -- Figure 6A-E --;

at column 4, line 17, please replace "Figure 7" with -- Figure 7A-B --;

at column 4, line 19, please replace "Figure 8" with -- Figure 8A-B --;

at column 4, line 21, please replace "Figure 9" with -- Figure 9A-E --;

at column 5, line 61, please replace "Figure 7" with -- Figure 7A-B --;

at column 6, line 1, please replace "Figure 8" with -- Figure 8A-B --;

at column 6, line 8, please replace "Figure 9" with -- Figure 9A-E --;

at column 6, line 59, please replace "hight" with -- high --;

at column 7, line 2, please replace "Figures 4, 5 and 6" with -- Figures 4A-C, 5A-B and 6A-E --;

UNITED STATES PATENT AND TRADEMARK OFFICE
CERTIFICATE OF CORRECTION

PATENT NO. : 5,981,193
APPLICATION NO. : 07/938154
DATED : November 9, 1999
INVENTOR(S) : Harpold et al.

It is certified that error appears in the above-identified patent and that said Letters Patent is hereby corrected as shown below:

at column 9, line 57, please replace "Figures 4, 5 and 6" with -- Figures 4A-C, 5A-B and 6A-E --;

at column 9, line 62, please replace "Figures 7, 8 and 9" with -- Figures 7A-B, 8A-B and 9A-E --;

at column 10, line 6, please replace "Figure 7" with -- Figure 7A-B --;

at column 10, line 8, please replace "Figure 8" with -- Figure 8A-B --;

at column 10, line 9, please replace "Figure 9" with -- Figure 9A-E --;

IN THE CLAIMS:

Please replace claim 3, column 25, lines 52-56 with the following claim:

-- 3. An isolated and purified human neuronal nicotinic acetylcholine receptor subunit encoded by the beta 2-encoding nucleic acid in a plasmid having all of the identifying characteristics of HnAChR$\hat{a}$2 deposited under ATCC Accession No. 68279. --

This certificate supersedes the Certificate of Correction issued October 28, 2008.

Signed and Sealed this

Eighteenth Day of November, 2008

JON W. DUDAS
*Director of the United States Patent and Trademark Office*